United States Patent
Bono et al.

(10) Patent No.: US 8,900,809 B1
(45) Date of Patent: Dec. 2, 2014

(54) **OLIGONUCLEOTIDES AND METHODS TO IDENTIFY SHIGA TOXIN CONTAINING *ESCHERICHIA COLI* SEROTYPES**

(75) Inventors: James L. Bono, Fairfield, NE (US); Keri N. Norman, Laredo, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 86 days.

(21) Appl. No.: 13/604,922

(22) Filed: Sep. 6, 2012

Related U.S. Application Data

(60) Provisional application No. 61/531,664, filed on Sep. 7, 2011.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
CPC .......... *C12Q 1/689* (2013.01); *C12Q 2600/156* (2013.01)
USPC ............................ 435/6.1; 435/91.1; 536/24.3

(58) Field of Classification Search
CPC .......................... C12Q 1/689; C12Q 2600/156
See application file for complete search history.

(56) References Cited

PUBLICATIONS

GM955627.1 (Genbank, NCBI, NLM, Dec. 2008).*

* cited by examiner

*Primary Examiner* — Jehanne Sitton
(74) *Attorney, Agent, or Firm* — John Fado; Albert Y. Tsui; Lesley Shaw

(57) ABSTRACT

Disclosed are oligonucleotides and methods related to identifying *Escherichia coli* serotypes by gene sequence polymorphisms. More specifically disclosed is oligonucleotides and methods to detecting a genotype of a single-nucleotide polymorphism in the O-antigen operon to identify Shiga toxin-producing serotypes O26, O111, O103, O145, O45, and O121.

6 Claims, 6 Drawing Sheets

Evaluation of Shiga toxigenic E. coli O26:H11 specific DNA markers with different sample matrixes.

| Sample | Dilution | rmlA 30 | wzx 953 | fnl1 88 |
|---|---|---|---|---|
| Water | Undiluted | - | Y[a] | Y |
| Water | $10^{-1}$ dilution | Y | Y | Y |
| Water | $10^{-2}$ dilution | Y | Y | Y |
| Water | $10^{-3}$ dilution | Y | - | - |
| Ground beef | Undiluted | Y | Y | Y |
| Ground beef | $10^{-1}$ dilution | Y | Y | Y |
| Ground beef | $10^{-2}$ dilution | Y | Y | Y |
| Ground beef | $10^{-3}$ dilution | Y | Y | Y |
| Spinach | Undiluted | - | Y | Y |
| Spinach | $10^{-1}$ dilution | - | Y | Y |
| Spinach | $10^{-2}$ dilution | - | Y | Y |
| Spinach | $10^{-3}$ dilution | Y | Y | Y |

[a] "Y" indicates a the sample was detected by the DNA marker.

FIG. 1

Evaluation of Shiga toxigenic O45:H2 specific DNA markers with different sample matrixes.

| Sample | Dilution | rmlB 966 | wbhQ 721 | wbhU 241 | wzy 752 | wzy 906 | wbhW 21 | wbhW 997 | inter 325 | inter 560 |
|---|---|---|---|---|---|---|---|---|---|---|
| Water | Undiluted | Y[a] | Y | Y | Y | Y | Y | Y | - | Y |
| Water | $10^{-1}$ dilution | Y | Y | Y | Y | Y | Y | Y | - | Y |
| Water | $10^{-2}$ dilution | Y | Y | Y | Y | Y | - | Y | - | Y |
| Water | $10^{-3}$ dilution | - | - | Y | - | Y | - | - | - | Y |
| Ground beef | Undiluted | Y | Y | Y | Y | Y | - | Y | - | Y |
| Ground beef | $10^{-1}$ dilution | Y | Y | Y | Y | Y | Y | Y | - | Y |
| Ground beef | $10^{-2}$ dilution | Y | Y | Y | Y | Y | Y | Y | - | Y |
| Ground beef | $10^{-3}$ dilution | Y | Y | Y | Y | Y | Y | Y | - | Y |
| Spinach | Undiluted | Y | Y | Y | Y | Y | - | Y | - | Y |
| Spinach | $10^{-1}$ dilution | Y | Y | Y | Y | Y | Y | Y | - | Y |
| Spinach | $10^{-2}$ dilution | Y | Y | Y | Y | Y | Y | Y | - | Y |
| Spinach | $10^{-3}$ dilution | Y | Y | Y | Y | Y | - | Y | - | Y |

[a] "Y" indicates a the sample was detected by the DNA marker.

FIG. 2

Evaluation of Shiga toxigenic *E. coli* O111:H8 specific DNA markers with different sample matrixes.

| Sample | Dilution | inter 219 | *wbdH* 1006 | *wbdK* 687 | *wzx* 1128 |
|---|---|---|---|---|---|
| Water | Undiluted | - | - | - | - |
| Water | 10⁻¹ dilution | Yª | Y | Y | Y |
| Water | 10⁻² dilution | Y | Y | Y | Y |
| Water | 10⁻³ dilution | Y | Y | Y | Y |
| Ground beef | Undiluted | Y | Y | Y | Y |
| Ground beef | 10⁻¹ dilution | Y | Y | Y | Y |
| Ground beef | 10⁻² dilution | Y | Y | Y | Y |
| Ground beef | 10⁻³ dilution | Y | Y | - | Y |
| Spinach | Undiluted | Y | Y | Y | Y |
| Spinach | 10⁻¹ dilution | Y | Y | Y | Y |
| Spinach | 10⁻² dilution | Y | Y | Y | Y |
| Spinach | 10⁻³ dilution | Y | Y | - | - |

ª "Y" indicates a the sample was detected by the DNA marker.

FIG. 3

Evaluation of Shiga toxigenic *E. coli* O103:H2 specific DNA markers with different sample matrixes.

| Sample | Dilution | *wbtD* 937 |
| --- | --- | --- |
| Water | Undiluted | Y[a] |
| Water | $10^{-1}$ dilution | Y |
| Water | $10^{-2}$ dilution | Y |
| Water | $10^{-3}$ dilution | Y |
| | | |
| Ground beef | Undiluted | Y |
| Ground beef | $10^{-1}$ dilution | Y |
| Ground beef | $10^{-2}$ dilution | - |
| Ground beef | $10^{-3}$ dilution | - |
| | | |
| Spinach | Undiluted | Y |
| Spinach | $10^{-1}$ dilution | Y |
| Spinach | $10^{-2}$ dilution | - |
| Spinach | $10^{-3}$ dilution | - |

[a] "Y" indicates a the sample was detected by the DNA marker.

FIG. 4

Evaluation of Shiga toxigenic *E. coli* O121:H19 specific DNA markers with different sample matrixes.

| Sample | Dilution | *vioA* 313 | *wbqE* 437 | *wbql* 582 |
|---|---|---|---|---|
| Water | Undiluted | Y[a] | Y | Y |
| Water | $10^{-1}$ dilution | Y | Y | Y |
| Water | $10^{-2}$ dilution | Y | Y | Y |
| Water | $10^{-3}$ dilution | Y | - | - |
| Ground beef | Undiluted | - | - | - |
| Ground beef | $10^{-1}$ dilution | Y | Y | Y |
| Ground beef | $10^{-2}$ dilution | Y | Y | Y |
| Ground beef | $10^{-3}$ dilution | Y | Y | Y |
| Spinach | Undiluted | Y | Y | Y |
| Spinach | $10^{-1}$ dilution | Y | Y | Y |
| Spinach | $10^{-2}$ dilution | Y | - | - |
| Spinach | $10^{-3}$ dilution | Y | Y | Y |

[a] "Y" indicates a the sample was detected by the DNA marker.

FIG. 5

Evaluation of Shiga toxigenic *E. coli* O145:NM specific DNA markers with different sample matrixes.

| Sample | Dilution | *wzy* 37 |
|---|---|---|
| Water | Undiluted | Y[a] |
| Water | $10^{-1}$ dilution | Y |
| Water | $10^{-2}$ dilution | Y |
| Water | $10^{-3}$ dilution | - |
| Ground beef | Undiluted | Y |
| Ground beef | $10^{-1}$ dilution | Y |
| Ground beef | $10^{-2}$ dilution | Y |
| Ground beef | $10^{-3}$ dilution | Y |
| Spinach | Undiluted | Y |
| Spinach | $10^{-1}$ dilution | Y |
| Spinach | $10^{-2}$ dilution | - |
| Spinach | $10^{-3}$ dilution | Y |

[a] "Y" indicates a the sample was detected by the DNA marker.

FIG. 6

OLIGONUCLEOTIDES AND METHODS TO IDENTIFY SHIGA TOXIN CONTAINING *ESCHERICHIA COLI* SEROTYPES

CROSS-REFERENCE TO RELATED APPLICATION

This present application claims priority under 35 U.S.C. §119(e) to U.S. Provisional Ser. No. 61/531,664, which was filed on Sep. 7, 2011, and is hereby incorporated by reference.

FIELD OF THE INVENTION

The invention generally relates to identifying *Escherichia coli* serotypes by gene sequence polymorphisms. More specifically, the field of invention relates to detecting a genotype of a single-nucleotide polymorphism in the O-antigen operon to identify Shiga toxin-producing serotypes O26, O111, O103, O145, O45, and O121.

BACKGROUND OF INVENTION

*Escherichia coli* have been recognized as an important human pathogen and major cause of diarrhea and hemorrhagic colitis. *E. coli* can be characterized into several different categories based on pathogenic features, including enteropathogenic (EPEC), enteroaggregative (EAEC), enteroinvasive (EIEC), enterotoxigenic (ETEC), and Shiga toxin-producing (STEC). Enterohemorrhagic *E. coli* (EHEC) are a subgroup within the STEC and these strains cause hemorrhagic colitis and severe disease in humans.

There are essentially two main types of Stxs: Stx/Stx1 and Stx2. Stx is produced from *Shigella dysenteriae* type 1, while Stx1 and Stx2 are produced from *Escherichia coli*. Stx and Stx1 are virtually identical, with only one amino acid difference in the A subunit. The mature A and B subunits of Stx1 and Stx2 have 68 and 73% similarity, respectively.

The majority of previous studies have focused on *E. coli* O157:H7 because this strain was most commonly linked to illness in the United States in the 1980's and 90's. However, outside of the United States non-O157 strains are often more prevalent and recently non-O157 strains have been linked to outbreaks and illness in the United States.

Cattle have been identified as potential reservoirs for *E. coli* and consequently raw milk and under-cooked ground beef have been implicated as sources of human infection. In 1994, the Food Safety and Inspection Service (FSIS) under the authority of the Federal Meat Inspection Act declared *E. coli* O-157:H7 to be an adulterant in ground beef and over the subsequent years new and revised protocols for O157:H7 testing in ground beef have been implemented. In 2000, non-O157 STEC became a reportable disease and there was a voluntary request for public health departments to report cases to the National Notifiable Diseases Surveillance System. A study conducted on non-O157 STEC infection in the United States from 1983 to 2002 found that 940 non-O157 STEC isolates had been submitted and confirmed by the Center for Disease Control and Prevention (CDC). The majority of the strains (71%) belonged to one of six major serogroups, including O111, O26, O103, O145, O45, and O121. Current research is focusing on these six strains to better understand the epidemiology in humans and cattle and develop accurate testing procedures. Understanding the epidemiology of these six strains is vital to developing methods to detect food products that been infected with Shiga toxin-producing *E. coli* strains.

It is difficult to report on the prevalence of non-O157 *E. coli* infections in the United States inasmuch as reporting is not mandatory. The non-mandatory reporting compounds the information gap for the various *E. coli* serogroups. The association between strains found in cattle and those causing human illness is further complicated because not all non-O157 *E. coli* found in cattle cause disease. Many strains of non-O157 *E. coli* in cattle lack Shiga toxin genes and therefore are not virulent to humans. It will be important to both the cattle industry as well as consumers to develop tests that not only identify non-O157 *E. coli* but also differentiate between virulent and non-virulent strains.

Given the inability to detect non-O157 *E. coli* Shiga toxin-producing serotypes, there is a need to develop constructs and methods to detect such serotypes to ensure food safety, particularly in vegetable produce and animal meat products. In order to prevent unnecessary loss of product and revenue, such test and assays that detect these serotypes need to be both fast and accurate, preferably in conjunction with RT-PCR techniques.

BRIEF SUMMARY OF THE INVENTION

The present invention is based, in part, on the discovery of a plurality of single nucleotide polymorphism (SNP) markers that are associated with various Shiga toxin producing *Escherichia coli*. Disclosed herein are oligonucleotide probes selected from the group consisting of SEQ ID Nos: 2, 5, 8, 11, 14, 17, 20, 23, 26, 29, 32, 35, 38, 41, 44, 47, 50, 53, 56, 59, 62, 65, and 68 that hybridize with the disclose single nucleotide polymorphisms.

Disclosed herein also is a method for determining whether a sample contains a Shiga toxin-producing *Escherichia coli* strain by detecting the presence of at least one polymorphism in a O-antigen operon encoding nucleic acid. In one embodiment of the invention the method to detect a Shiga toxin producing *E. coli* strain comprises the steps of providing a nucleic acid sample, contacting the sample with at least one forward amplification primer and at least one reverse amplification primer, amplifying a segment of the O-antigen operon encoding nucleic acid of the sample to form an amplified product, and detecting the presence of the amplified product, wherein the presence of the amplified product indicates the presence of a Shiga toxin producing isolate *Escherichia coli* strain. In one aspect of the invention, the method detects Shiga toxin-producing. *coli* strains from a meat product. In another aspect of the invention, the method detects Shiga toxin-producing *E. coli* strains from a vegetable product. In yet another aspect of the invention, the method detects Shiga toxin production *E. coli* strains serotype O26, O111, O103, O145, O45, or O121.

Disclosed herein also is a method for determining whether a sample contains a Shiga toxin-producing *Escherichia coli* strain by detecting the presence of at least one polymorphism in a O-antigen operon encoding nucleic acid, the method comprising providing a nucleic acid sample, contacting the sample with at least one forward amplification primer and at least one reverse amplification primer, amplifying a segment of the O-antigen operon encoding nucleic acid of the sample to form an amplified product, wherein the amplified product is hybridized with an oligonucleotide selected from a group consisting of SEQ. ID Nos: 2, 5, 8, 11, 14, 17, 23, 26, 29, 32, 41, 44, 47, 50, 53, 56, 59, 62, 65, and 68 with the oligonucleotide bound by said amplification primers; and detecting the presence of the amplified product, wherein the presence of the amplified product indicates the presence of a Shiga toxin producing isolate *Escherichia coli* strain.

In another embodiment of the invention, disclosed is a method for determining whether a sample has a Shiga toxin-producing *Escherichia coli* strain serotype O26, the method comprising detecting in a nucleic acid sample isolated from a sample a genotype indicative of Shiga toxin-producing *Escherichia coli* serotype O26, wherein the genotype comprises a T at position 30 of SEQ ID NO: 70 (rmlA), a G at position 953 of SEQ ID NO: 71 (wzx), or an A at position 88 of SEQ ID NO: 72 (fll), wherein the detection of the genotype is indicative of Shiga toxin-producing *Escherichia coli* serotype O26. In one embodiment of the invention, a genotype comprising a T at position 30 of SEQ ID NO: 70 (rmlA) and a G at position 953 of SEQ ID NO: 71 (wzx) is indicative of Shiga toxin-producing *Escherichia coli* serotype O26. In another embodiment of the invention, a genotype comprising a G at position 953 of SEQ ID NO: 71 (wzx) and an A at position 88 of SEQ ID NO: 72 (fnl1) is indicative of Shiga toxin-producing *Escherichia coli* serotype O26.

In another embodiment of the invention, disclosed is a method for determining whether a sample has a Shiga toxin-producing *Escherichia coli* strain serotype O45, the method comprising detecting in a nucleic acid sample isolated from a sample a genotype indicative of Shiga toxin-producing *Escherichia coli* serotype O45, wherein the genotype comprises a C at position 966 of SEQ ID NO: 73 (rmlB), an A at position 721 of SEQ ID NO: 74 (wbhQ), an A at position 241 of SEQ ID NO: 75 (wbhU), a T at position 543 of SEQ ID NO: 75 (wbhU), a C at position 752 of SEQ ID NO: 76 (wzy), a C at position 906 of SEQ ID NO: 76 (wzy), a T at position 21 of SEQ ID NO: 77 (whbW), a G at position 997 of SEQ ID NO: 77 (wbhW), an A at position 325 of SEQ ID NO: 78 (intergenic region), an A at position 366 of SEQ ID NO: 78 (intergenic region), or a C at position 560 of SEQ ID NO: 78 (intergenic region).

In yet another embodiment of the invention, disclosed is a method for determining whether a sample has a Shiga toxin-producing *Escherichia coli* strain serotype O103, the method comprising detecting in a nucleic acid sample isolated from a sample a nucleotide occurrence of a single nucleotide polymorphism at position 937 of SEQ ID NO: 79 (wbtD), wherein the detection of the single nucleotide polymorphism is indicative of Shiga toxin-producing *Escherichia coli* serotype O103. In one embodiment of the invention, a single nucleotide polymorphism is a T at position 937 of SEQ ID NO: 79 (wbtD) is indicative of Shiga toxin-producing *Escherichia coli* serotype O103.

In another embodiment of the invention, disclosed is a method for determining whether a sample has a Shiga toxin-producing *Escherichia coli* strain serotype O145, the method comprising detecting in a nucleic acid sample isolated from a sample a nucleotide occurrence of a single nucleotide polymorphism at position 37 of SEQ ID NO: 80 (wyz), wherein the detection of the single nucleotide polymorphism is indicative of Shiga toxin-producing *Escherichia coli* serotype O145. In one embodiment of the invention, a single nucleotide polymorphism is a C at position 37 of SEQ ID NO: 80 (wyz) is indicative of Shiga toxin-producing *Escherichia coli* serotype O145.

In another embodiment of the invention, disclosed is a method for determining whether a sample has a Shiga toxin-producing *Escherichia coli* strain serotype O111, the method comprising detecting in a nucleic acid sample isolated from a sample a genotype indicative of Shiga toxin-producing *Escherichia coli* serotype O111, wherein the genotype comprises a T at position 219 of SEQ ID NO: 81 (intergenic region), an A at position 1006 of SEQ ID NO: 82 (wbdH), a T at position 687 of SEQ ID NO: 83 (wbdK), or a T at position 1128 of SEQ ID NO: 84 (wzx), wherein the detection of the genotype is indicative of Shiga toxin-producing *Escherichia coli* serotype O111.

In yet another embodiment of the invention, disclose is a method for determining whether a sample has a Shiga toxin-producing *Escherichia coli* strain serotype O121, the method comprising detecting in a nucleic acid sample isolated from a sample a genotype indicative of Shiga toxin-producing *Escherichia coli* serotype O121, wherein the genotype comprises a T at position 313 of SEQ ID NO: 85 (vioA), a T at position 437 of SEQ ID NO: 86 (wbqE), or an A at position 582 of SEQ ID NO: 87 (wbqI), wherein the detection of the genotype is indicative of Shiga toxin-producing *Escherichia coli* serotype O121.

BRIEF DESCRIPTION OF THE DRAWING

The present invention together with the above and other objects and advantages may best be understood from the following detailed description of the embodiment of the invention illustrated in the drawings, wherein:

FIG. 1 is a table depicting the detection of shiga toxigenic *E. coli* O26:H11 with various oligonucleotides (SEQ ID Nos.: 1, 2, 3, and 4, 5, 6, and 4, 5, 6, and 7, 8, 9) in a plurality of samples.

FIG. 2 is a table depicting the detection of shiga toxigenic *E. coli* O45:H2 with various oligonucleotides (SEQ ID Nos: 10, 11, 12, and 13, 14, 15, and 16, 17, 18, and 19, 20, 21, and 22, 23, 24, and 25, 26, 27, and 28, 29 30, and 31, 32, 33, and 40, 41, 42) in a plurality of samples.

FIG. 3 is a table depicting the detection of shiga toxigenic *E. coli* O111:H8 with various oligonucleotides (SEQ ID Nos.: 49, 50, 51, or 52, 53, 54, or 55, 56, 57, or 58, 59, 60) in a plurality of samples.

FIG. 4 is a table depicting the detection of shiga toxigenic *E. coli* O103:H2 with various oligonucleotides (SEQ ID Nos: 43, 44, 45) in a plurality of samples.

FIG. 5 is a table depicting the detection of shiga toxigenic *E. coli* O121:H19 with various oligonucleotides (SEQ ID Nos: 61, 62, 63, or 64, 65, 66, or 67, 68, 69) in a plurality of samples.

FIG. 6 is a table depicting the detection of shiga toxigenic *E. coli* O145:NM with an oligonucleotides (SEQ ID Nos: 46, 47, 48) in a plurality of samples.

DETAILED DESCRIPTION OF THE INVENTION

Definition

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

As used herein, the acronym "STEC" refers to Shiga toxin-producing *Escherichia coli*.

The present invention is based in part on the discovery of single nucleotide polymorphisms (SNPs) that can be used to distinguish between the Shiga-toxin producing alleles and thus Shiga-toxin producing *E. coli* serotypes. Accordingly, provided herein are methods for generating such information from a nucleic acid sample obtained from *E. coli* containing biological sample, by identifying in the sample, a nucleotide occurrence for at least one single nucleotide polymorphism (SNP), wherein the nucleotide occurrence is associated with the Shiga toxin producing genotype. For example, the methods can be used to identify Shiga toxin producing alleles of *Escherichia coli* serotypes including, but not limited to O26, O111, O103, O145, O45, and O121.

Since genomic DNA is double-stranded, each SNP can be defined in terms of either the plus strand or the minus strand. Thus, for every SNP, one strand will contain an immediately 5'-proximal invariant sequence and the other strand will contain an immediately 3'-distal invariant sequence. In one embodiment, and using the FSIS O26 amplicon alignment as an example, a SNP of the present invention can be identified, in part, by its position at nucleotide 30 set forth in SEQ ID NO: 70. (see Table 3, infra) in a target nucleic acid sequence. In another embodiment, a SNP of the invention can be identified as present in a nucleic acid sequence resulting from the replication of a nucleic acid sequence by any one of forward oligonucleotide primers in combination with any one of reverse oligonucleotide primers with the probe sequence (see e.g., Table 2, infra).

Nucleic acid molecules having a sequence complementary to that of an immediately 3'-distal invariant sequence of a SNP can, if extended in a "template-dependent" manner, form an extension product that would contain the SNP's polymorphic site. A preferred example of such a nucleic acid molecule is a nucleic acid molecule whose sequence is the same as that of a 5'-proximal invariant sequence of the SNP. "Template-dependent" extension refers to the capacity of a polymerase to mediate the extension of a primer such that the extended sequence is complementary to the sequence of a nucleic acid-template. A "primer" is a single-stranded oligonucleotide (or oligonucleotide analog) or a single-stranded polynucleotide (or polynucleotide analog) that is capable of being extended by the covalent addition of a nucleotide (or nucleotide analog) in a "template-dependent" extension reaction. In order to possess such a capability, the primer must have a 3'-hydroxyl (or other chemical group suitable for polymerase mediated extension) terminus, and be hybridized to a second nucleic acid molecule (i.e. the "template"). A primer is generally composed of a unique sequence of eight bases or longer complementary to a specific region of the target molecule such that the 3' end of the primer is immediately proximal to a target nucleotide of interests. Typically, the complementary region of the primer is from about 30 bases to about 36 bases.

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term genotyping or genotype refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. Each allele may be present at a different frequency in a given population, for example 30% of the chromosomes in a population may carry the A allele and 70% the C allele. The frequency of the A allele would be 30% and the frequency of the C allele would be 70% in that population.

The Example provided herein illustrates the use of genotyping analysis to identify SNPs that can be used to determine whether a biological sample possesses a genotype associated with Shiga toxin producing phenotypes. The SNP alleles contained in a Shiga toxin genotypes can be determined using extension oligonucleotide primers (SEQ ID NOS:1-69) to identify particular SNPs in a target nucleic acid sequence. In some embodiments, forward oligonucleotide primers (SEQ ID NOS:1, 4, 7, 10, 13, 16, 19, 22, 25, 28, 31, 34, 37, 40, 43, 46, 49, 52, 55, 58, 61, 64, 67) and reverse oligonucleotide primers (SEQ ID NOS: 3, 6, 9, 12, 15, 18, 21, 24, 27, 30, 33, 36, 39, 42, 45, 48, 51, 54, 57, 60, 63, 69) were used to amplify specific target sequences prior to extension.

The oligonucleotide primer sequences listed in Table 2 can be used as sets of oligonucleotides. For example, the set of oligonucleotides useful for identifying marker O26 rmlA 30 includes SEQ ID NO:1, SEQ ID NO:2 and SEQ ID NO:3, or any combination thereof. Detection of a single nucleotide polymorphism (SNP) is detected at the 3' end of the probe, where in the presence of a SNP an addition of a nucleotide will cause an increase in probe mass indicating the presence of the SNP.

With respect to the probe and the teaching of the SNPs disclosed herein, a person having ordinary skill in the art will be able to construct other probes to detect the SNPs disclosed herein. For example, the construction of TaqMan probes wherein the SNP is incorporated in the probe to genotype a SNP from a sample.

SEQ ID NO:1 (forward primer) and SEQ ID NO:3 (reverse primer) can be used to amplify the sequence containing the marker prior to detection. Thus, each set of oligonucleotide primers provides the means for detecting at least one genetic marker useful for determining the genotype of a subject organism. Thus, the "marker set" of oligonucleotide primers for marker comprises SEQ ID NO:1, SEQ ID NO:2 and SEQ ID NO:3. Such a set of oligonucleotides can be designated "marker set O26 rmlA 30". In addition, the oligonucleotides useful for amplifying a target nucleic acid sequence would include a "primer pair" such as SEQ ID NO:1 and SEQ ID NO:3. A "primer pair" includes a forward and reverse oligonucleotide primer while a "marker set" would include a forward, a reverse and an extension oligonucleotide primer.

Table 2 provides primer sequences (See "Forward" and "Reverse") that were used to amplify a region that includes the SNP, and amplicon sequences that indicate the nucleotide occurrences for the SNP that were identified in parenthesis within the amplicon sequences provided in Table 2.

Polymorphisms are allelic variants that occur in a population that can be a single nucleotide difference present at a locus, or can be an insertion or deletion of one, a few or many consecutive nucleotides. As such, a single nucleotide polymorphism (SNP) is characterized by the presence in a population of one or two, three or four nucleotides (i.e., adenosine, cytosine, guanosine or thymidine), typically less than all four nucleotides, at a particular locus in a genome. It will be recognized that, while the methods of the invention are exemplified primarily by the detection of SNPs, the disclosed methods or others known in the art similarly can be used to identify other types of polymorphisms, which typically involve more than one nucleotide.

The polynucleotide or an oligonucleotide of the invention can further include a detectable label. For example, the detectable label can be associated with the polynucleotide at a position corresponding to the SNP position, or the complement thereof, of any one of SEQ ID NO: 2. As discussed in more detail herein, the labeled polynucleotide can be generated, for example, during a micro sequencing reaction, such as SNP-IT reaction. Detectable labeling of a polynucleotide or oligonucleotide is well known in the art. Particular non-limiting examples of detectable labels include chemiluminescent labels, fluorescent labels, radiolabels, enzymes, or even unique oligonucleotide sequences.

In another embodiment, the present invention provides an isolated vector that includes a polynucleotide or oligonucleotide disclosed herein. The term "vector" refers to a plasmid, virus or other vehicle known in the art that has been manipulated by insertion or incorporation of a nucleic acid sequence. Methods that are well known in the art can be used to construct vectors, including in vitro recombinant DNA techniques, synthetic techniques, and in vivo recombination/genetic techniques (See, for example, the techniques described in Maniatis et al. 1989 Molecular Cloning A Laboratory Manual, Cold Spring Harbor Laboratory, New York, incorporated herein in its entirety by reference).

In another aspect, the present invention provides a primer pair comprising any one of SEQ ID NOS: 1, 4, 7, 10, 13, 16, 19, 22, 25, 28, 31, 34, 37, 40, 43, 46, 49, 52, 55, 58, 61, 64, 67 as a first (forward) primer and any one of SEQ ID NOS: 3, 6, 9, 12, 15, 18, 21, 24, 27, 30, 33, 36, 39, 42, 45, 48, 51, 54, 57, 60, 63, 69 as a second (reverse) oligonucleotide primer. A primer pair will prime polynucleotide synthesis of a target nucleic acid region.

The examples are for the purpose of illustrating an embodiment and are not to be construed as limitations.

EXAMPLE 1

Sampling

A sample of 164 non-O157 *E. coli* strains isolated from various sources and geographic areas were surveyed for nucleotide polymorphism in the O-antigen operon. These include sixty-four O26, forty-seven O111, twenty-three O103, six O145, twelve O45, and twelve O121 strains. The samples originated from a variety of sources including humans, cattle, sheep, goats, swine, turkey, chickens, dogs, whitetail deer, flies, and environmental surfaces. Geographical data provided for a number of the strains found that the isolates were from several states including CA, CO, DE, FL, IA, ID, 1N, KS, LA, NE, NH, NJ, OK, SD, TN, TX, UT, WI, and WS. There were also several international strains from Switzerland, Germany, Australia, England, Kenya, Peru, Italy, Brazil, Guatam, Denmark, Canada, Cuba, and Japan.
DNA Isolation A single representative colony from each isolate was inoculated into 10 ml of Luria broth and incubated overnight at 37° C. on a shaker. Genomic DNA was extracted using the Qiagen Genomic-tip 100/G columns (Valencia, Calif.) and techniques previously described [33]. DNA concentration was determined with a spectrophotometer (Nano-Drop technologies, Wilmington, Del.) and diluted with Tris-EDTA (TE; 0.5×, 1M Tris pH 8, 0.5M EDTA) to a 5 ng/µl working solution.
PCR, DNA Sequencing, and Analysis Identification of single nucleotide polymorphisms was accomplished by polymerase chain reaction (PCR) of short fragments of DNA followed by genetic sequencing. The O-antigen operon was amplified for all of the strains using six to nine different PCR primer pairs along the entire length of the operon. Each of the PCR fragments were on average 1500 to 2000 base pairs in length and fragments overlapped by approximately 500 base pairs. Amplification reactions contained 3.2 µl dNTPs (1.25 mM, promega, Madison, Wis.), 2 µl 10× Buffer (HotStarTaq DNA Polymerase kit, Qiagen), 0.1 µl HotStarTaq DNA Polymerase (5 U/µl, Qiagen), 0.2 µl of each primer (30 µM), and 1 µl template DNA in a 20 µl reaction volume. Amplification was performed using a S1000 or Peltier Dyad BIO-RAD (Hercules, Calif.) thermocycler under the following conditions: an initial denaturation step at 95° C. for 15 minutes followed by 30 seconds at 94° C., 30 seconds at 52° C., and 2 minutes at 72° C. for 35 cycles, and a final extension step at 72° C. for 10 minutes. Amplification was verified by running PCR products on a 1% agarose gel containing ethidium bromide.

DNA sequencing reactions were set up using a modified 2.0 Big Dye protocol (Applied Biosystems, Carlsbad, Calif.). For the initial reaction, 5.5 µl of the PCR product and 7 µl ExoI (0.1 U/µl) were added to each well. Reactions were run on a Peltier Dyad BIO-RAD thermocycler under the following conditions: hold at 37° C. for one hour, followed by 20 minutes at 65° C. Following the reaction in the thermocycler, 23 µl of 100% ETOH was added to each well and centrifuged at 3200 rpm for 30 minutes at room temperature. The plate was inverted and centrifuged briefly at 500 rpm and allowed to dry at room temperature for at least 30 minutes. The sequencing reaction mix contained 0.25 µl Big Dye, 1.75 µl 5× buffer, and 0.11 µl primer (30 µM), for a final volume of 5 µl per well. Reactions were run on a Peltier Dyad BIO-RAD thermocycler under the following conditions: for 25 cycles, 30 seconds at 96° C., 2.5 second ramp to 96° C., 10 seconds at 96° C., 2.5 second ramp to 50° C., 5 seconds at 50° C., 2.5 second ramp to 60° C., and 4 minutes at 60° C. The plates were precipitated as follows: add 22 µl 70% isopropanol to each well, centrifuge for 30 minutes at 3200 rpm, briefly centrifuge upside down at 500 rpm, add 22 µl 70% ETOH, centrifuge for 30 minutes at 3200 rpm, briefly centrifuge upside down at 500 rpm, and allow to air dry for at least 10 minutes. Plates were stored at −20° C. until they were placed on the sequencing machine. DNA sequences were determined using a 3730xl DNA analyzer (Applied Biosystems, Carlsbad, Calif.).

DNA sequences were analyzed and assembled using Geneious Pro version 5.3.6. (Biomatters Ltd.) Assembled sequences of the O-antigen operon were aligned and compared to a reference sequence using the MUSCLE alignment feature in Geneious and unweighted pair group method with arithmetic mean (UPGMA) trees with bootstrap values generated from the results.
PCR of Virulence Genes PCR of stx1, stx2, eaeA, and hlyA was performed with a multiplex PCR assay. Amplification reactions contained 1 µl of template DNA, 10.05 µl molecular grade water (Eppendorf, Hauppauge, N.Y.), 3.0 µl 10× buffer (HotStarTaq DNA Polymerase Kit, Qiagen), 3.6 µl MgC12 (25 mM, HotStarTaq DNA Polymerase Kit, Qiagen), 12.0 µl dNTP (1.25 mM, Promega), 0.30 µl of each primer (30 µM), and 0.15 µl of HotStarTaq DNA Polymerase (5 U/µl, Qiagen). Reactions were run on a Peltier Dyad BIO-RAD thermocycler under the following conditions: an initial degradation at 95° C. for 15 minutes, followed by 60 seconds at 94° C., 60 seconds at 53° C., and 60 seconds at 72° C. for 35 cycles, and a final extension step at 72° C. for ten minutes. Amplification was verified by running PCR products on a 1% agarose gel containing ethidium bromide.
Validation of SNP's Polymorphisms were genotyped by matrix-assisted laser desorption-ionization time-of-flight (MALDI-TOF) genotyping (Sequenom, Inc., San Diego, Calif., USA). MALDI-TOF assay and multiplexing design was conducted with MassARRAY® assay design software as recommended by the manufacturer (Sequenom, Inc.). Up to 36 polymorphisms were accepted for each multiplex and the assays were conducted with iPLEX Gold® chemistry on a MassARRAY® genotyping system per instructions of the manufacturer (Sequenom Inc.). "High confidence" genotype calls by the Genotyper® software were accepted as correct. "Aggressive" calls were inspected manually and verified as needed by Sanger Sequencing or replicate MALDI-TOF assays. A total of 768 strains were used to validate the SNP's and included one hundred ninety-two O157:H7, three O157:non-H7, four O55:H7, two O55:H6, eighty-three O111 STEC, twenty-three O111 non-STEC, eighty O26 STEC, thirty O26 non-STEC, nine O45 STEC, three O45 non-STEC, twenty-four O103 STEC, seven O103 non-STEC, five O145 STEC, one O145 non-STEC, six O121 STEC, six O121 non-STEC, eleven other *E. coli* STEC, one hundred seventy-six O-antigen standards, sixty-one *Salmonella*, and 42 other bacterium. Sensitivity and specificity estimates were calculated with exact 95% confidence intervals for each of the assays targeting the single nucleotide polymorphisms. The calculations were based on a binary outcome of the STEC or non-STEC allele. All isolates with the STEC allele were considered test positive, whereas test negative was any isolate with the alternate allele, an indecisive allele call, or no allele call. The test results were compared to three different known gene combinations; those containing a stx gene (STEC), those containing a stx gene and the eae gene (STEC with eae gene)), and those containing both a stx gene and the eae and hlyA genes (STEC with eae and hlyA genes).

EXAMPLE 2

Identification of SNP's

Three SNP's were identified in the 11,706 bp sequenced O-antigen operon of sixty-five O26 isolates (64 and 1 reference strain) that differentiated strains that contained Shiga toxins (STEC). The first is the rmlA 30 G>T polymorphism, the second is the wzx 953 T>G polymorphism, and the third is the fnI 1 88 G>A polymorphism. The rmlA 30 G>T and fnl1 88 G>A polymorphisms are found in the same strains and capture the majority of the STEC strains; however, the wzx 953 T>G polymorphism was needed to include a small subset of the isolates that only contain stx2. A combination of either rmlA 30 G>T or fnl1 88 G>A with wzx 953 T>G captured all of the STEC isolates in our collection that contained either stx1, stx2, or both stx1 and stx2. There were two isolates included with the STEC SNP that did not contain either stx1 or stx2.

In the 14,483 bp sequenced O-antigen operon of the thirteen O45 isolates (12 and 1 reference strain), eleven SNP's were identified that differentiated STEC strains. The first is the rmlB 966 T>C polymorphism, the second is the wbhQ 721 C>A polymorphism, the third is the wbhU 241 G>A polymorphism, the fourth is the wbhU 543 C>T polymorphism, the fifth is the wzy 752 T>C polymorphism, the sixth is the wzy 906 T>C polymorphism, the seventh is the wbhW 21 C>T polymorphism, the eighth is the wbhW 997 T>G polymorphism, the ninth is the intergenic 325 C>A polymorphism, the tenth is the intergenic 366 "A" base insertion, and the eleventh the intergenic 560 A>C polymorphism. A combination of any of the polymorphisms with the base insertion divided the O45 isolates in our collection into one group that contained isolates with stx1 and a second group containing isolates that did not contain stx1 or stx2.

Among the twenty-five O103 isolates (23 and 2 reference strains), one SNP was identified in the 11,881 bp sequenced O-antigen operon that differentiated STEC strains. The wbtD 937 C>T polymorphism captured all O103 isolates in our collection that contain stx (all of our O103 strains only contain stx1); however, it also included two strains that do not contain stx1 or stx2.

One SNP was identified in the 15,556 bp sequenced O-antigen operon in the eight O145 isolates (6 and 2 reference strains). The wyz 37 A>C polymorphism captured the O145 strains with only stx1 and also the strain with only stx2.

Four SNP's were identified in the 14,514 bp sequenced O-antigen operon in the forty-eight O111 isolates (47 and 1 reference strain) that differentiated the STEC strains. The first is the intergenic 219 G>T polymorphism, the second is the wbdH 1006 G>A polymorphism, the third is the wbdK 687 C>T polymorphism, and the fourth is the wzx 1128 A>T polymorphism. All four of the SNP's are found in the O111 STEC isolates and only one of the SNP's is needed to differentiate STEC isolates. The STEC SNP's capture all of the O111 isolates in our collection with either only stx1 or both stx1 and stx2 (there were no isolates with only stx2); however, there are three isolates included with the STEC SNP that do not contain stx1 or stx2.

In the 14,999 bp sequenced O-antigen operon in the thirteen O121 isolates (12 and 1 reference strain), there were three SNP's identified that differentiated the STEC strains. The first is the vioA 313 C>T polymorphism, the second is the wbqE 437 C>T polymorphism, and the third is the wbqI 582 G>A polymorphism. All three of these SNP's are found in O121 STEC isolates and only one of the SNP's is needed to differentiate the STEC isolates. The STEC SNP is able to capture all of the O121 strains containing only stx2; however, the STEC SNP does not capture the strains containing only stx1. It is interesting to note that the O121 strains with only stx1 do not contain eae or hlyA.

EXAMPLE 3

Validation of SNP's

Table 1 displays the sensitivity and specificity estimates for the 20 assays for STEC isolates, STEC isolates with the eae gene, and STEC isolates with the eae and hlyA genes.

Three probes were tested for the SNP's discovered in the O26 isolates. The sensitivity and specificity estimates are based on the use of both SNP's in conjunction. The first estimate is for the probes of the rmlA 30 G>T polymorphism with the wzx 953 T>G polymorphism and had a sensitivity of 95.2% (85.8, 98.8) and a specificity of 43.7% (40.0, 47.4) for O26 STEC isolates. The second estimate is for the probes of the fnlI 88 G>A polymorphism with the wzx 953 T>G polymorphism and had a sensitivity of 95.2% (85.8, 98.8) and a specificity of 85.6% (82.8, 88.1) for O26 STEC isolates. The sensitivity and specificity estimates for STEC isolates that have the eae gene and STEC isolates with the eae and hlyA genes are shown in Table 1.

Nine probes were tested for the SNP's discovered in the O45 isolates. The first probe targeted the rmlB 966 T>C polymorphism and had a sensitivity of 100% (62.9, 100) and a specificity of 97.4% (95.9, 98.3) for O45 STEC isolates. The second probe targeted the wbhQ 721 C>A polymorphism and had a sensitivity of 100% (62.9, 100) and a specificity of 99.1% (98.0, 99.6) for O45 STEC isolates. The third probe targeted the wbhU 241 G>A polymorphism had a sensitivity of 100% (62.9, 100) and a specificity of 95.5% (93.7, 96.8) for O45 STEC isolates. The fourth probe targeted the wzy 752 T>C polymorphism and had a sensitivity of 33.3% (9.0, 69.1) and specificity of 99.3% (98.4, 99.8) for O45 STEC isolates. The fifth probe targeted the wzy 906 T>C polymorphism and had a sensitivity of 100% (62.9, 100) and a specificity of 98.6% (97.3, 99.2) for O45 STEC isolates. The sixth probe targeted the wbhW 21 C>T polymorphism and had a sensitivity of 100% (62.9, 100) and a specificity of 98.6% (97.3, 99.2) for O45 STEC isolates. The seventh probe targeted the wbhW 997 T>G polymorphism and had a sensitivity of 100% (62.9, 100) and a specificity of 98.3% (97.0, 99.0) for O45 STEC isolates. The eighth probe targeted the intergenic 325 C>A polymorphism and had a sensitivity of 100% (62.9, 100) and a specificity of 96.7% (95.1, 97.8) for O45 STEC isolates. The ninth probe targeted the intergenic 560 A>C polymorphism and had a sensitivity of 100% (62.9, 100) and a specificity of 98.6% (97.3, 99.2) for O45 STEC isolates. The sensitivity and specificity estimates for STEC isolates with the eae gene and STEC isolates with the eae and hlyA genes are shown in Table 1.

One probe was tested for the SNP discovered in the O103 isolates. The probe targeted the wbtD 937 C>T polymorphism and had a sensitivity of 100% (80.0, 100) and a specificity of 99.5% (98.5, 99.8) for O103 STEC isolates. The sensitivity and specificity estimates for STEC isolates with the eae gene and STEC isolates with the eae and hlyA genes are shown in Table 1.

One probe was tested for the SNP discovered in the O145 isolates. The probe targeted the wzy 37 A>C polymorphism and had a sensitivity of 100% (46.3, 100) and a specificity of 98.8% (97.9, 99.5%) for O145 STEC isolates. The sensitivity and specificity estimates for STEC isolates with the eae gene and STEC isolates with the eae and hlyA genes are shown in Table 1.

Four probes were tested for the SNP's discovered in the O111 isolates. The first probe targeted the intergenic 219 G>T polymorphism and had a sensitivity of 84.4% (74.0, 91.3) and a specificity of 90.9% (88.4, 92.9) for O111 STEC isolates. The second probe targeted the wbdH 1006 G>A polymorphism and had a sensitivity of 93.5% (84.8, 97.6) and a specificity of 30.6% (27.2, 34.2) for O111 STEC isolates. The third probe targeted the wbdK 687 C>T polymorphism and had a sensitivity of 97.4% (90.1, 99.5) and a specificity of 92.2% (89.8, 94.0) for O111 STEC isolates. The fourth probe targeted the wzx 1128 A>T polymorphism and had a sensitivity of 97.4% (90.1, 99.5) and a specificity of 90.4% (87.9, 96.5) for O111 STEC isolates. The sensitivity and specificity estimates for STEC isolates with the eae gene and STEC isolates with the eae and hlyA genes are shown in Table 1.

Three probes were tested for the SNP's discovered in the O121 isolates. The first targeted the vioA 313 C>T polymorphism and had a sensitivity of 77.8% (40.2, 96.1) and a specificity of 99.7% (98.9, 100.0) for O121 STEC isolates. The second targeted the wbaE 437 C>T polymorphism and had a sensitivity of 77.8% (40.2, 96.1) and a specificity of 98.8% (97.7, 99.4) for O121 STEC isolates. The third targeted the wbql 582 G>A polymorphism and had a sensitivity of 77.8% (40.2, 96.1) and a specificity of 99.6% (98.7, 99.9) for O121 STEC isolates. The sensitivity and specificity estimates for STEC isolates with the eae gene and STEC isolates with the eae and hlyA genes are shown in Table 1.

TABLE 1

Sensitivity and specificity estimates for the 20 assays targeting the single nucleotide polymorphisms in the 6 O-serotypes.

| Assay | STEC[a] | | STEC with eae[b] | | STEC with eae and hly[c] | |
|---|---|---|---|---|---|---|
| | Se[d] (95% CI) | Sp[e] (95% CI) | Se (95% CI) | Sp (95% CI) | Se (95% CI) | Sp (95% CI) |
| O26 | | | | | | |
| rmlA 30 and wzx 953 | 95.2% (85.8, 98.8) | 43.7% (40.0, 47.4) | 95.1% (85.4, 98.7) | 43.5% (39.9, 47.3) | 94.8% (84.7, 98.7) | 43.4% (39.7, 47.1) |
| fml1 88 and wzx 953 | 95.2% (85.8, 98.8) | 85.6% (82.8, 88.1) | 95.1% (85.4, 98.7) | 85.4% (82.5, 87.9) | 94.8% (84.7, 98.7) | 85.0% (82.1, 87.5) |
| O45 | | | | | | |
| rmlB 966 | 100.0% (62.9, 100.0) | 97.4% (95.9, 98.3) | 100.0% (62.9, 100.0) | 97.4% (95.9, 98.3) | 100.0% (59.8, 100.0) | 97.2% (95.7, 98.2) |
| wbhQ 721 | 100.0% (62.9, 100.0) | 99.1% (98.0, 99.6) | 100.0% (62.9, 100.0) | 99.1% (98.0, 99.6) | 100.0% (59.8, 100.0) | 98.9% (97.9, 99.5) |
| wbhU 241 | 100.0% (62.9, 100.0) | 95.5% (93.7, 96.8) | 100.0% (62.9, 100.0) | 95.5% (93.7, 96.8) | 100.0% (59.8, 100.0) | 95.4% (93.6, 96.7) |
| wzy 752 | 33.3% (9.0, 69.1) | 99.3% (98.4, 99.8) | 33.3% (9.0, 69.1) | 99.3% (98.4, 99.8) | 37.5% (10.2, 74.1) | 99.3% (98.4, 99.8) |
| wzy 906 | 100.0% (62.9, 100.0) | 98.6% (97.3, 99.2) | 100% (62.9, 100.0) | 98.6% (97.3, 99.2) | 100.0% (59.8, 100.0) | 98.4% (97.2, 99.1) |
| wbhW 21 | 100.0% (62.9, 100.0) | 98.6% (97.3, 99.2) | 100.0% (62.9, 100.0) | 98.6% (97.3, 99.2) | 100.0% (59.8, 100.0) | 98.4% (97.2, 99.1) |
| wbhW 997 | 100.0% (62.9, 100.0) | 98.3% (97.0, 99.0) | 100.0% (62.9, 100.0) | 98.3% (97.0, 99.0) | 100.0% (59.8, 100.0) | 98.2% (96.9, 98.9) |
| inter 325 | 100.0% (62.9, 100.0) | 96.7% (95.1, 97.8) | 100.0% (62.9, 100.0) | 96.7% (95.1, 97.8) | 100.0% (59.8, 100.0) | 96.6% (95.0, 97.7) |
| inter 560 | 100.0% (62.9, 100.0) | 98.6% (97.3, 99.2) | 100.0% (62.9, 100.0) | 98.6% (97.3, 99.2) | 100.0% (59.8, 100.0) | 98.4% (97.2, 99.1) |
| O103 | | | | | | |
| wbtD 937 | 100.0% (80.0, 100.0) | 99.5% (98.5, 99.8) | 100.0% (79.1, 100.0) | 99.5% (98.5, 99.8) | 100.0% (79.1, 100.0) | 99.5% (98.5, 99.8) |

TABLE 1-continued

Sensitivity and specificity estimates for the 20 assays targeting the
single nucleotide polymorphisms in the 6 O-serotypes.

| Assay | STEC[a] | | STEC with eae[b] | | STEC with eae and hly[c] | |
|---|---|---|---|---|---|---|
| | Se[d] (95% CI) | Sp[e] (95% CI) | Se (95% CI) | Sp (95% CI) | Se (95% CI) | Sp (95% CI) |
| O111 | | | | | | |
| inter 219 | 84.4% (74.0, 91.3) | 90.9% (88.4, 92.9) | 81.3% (69.2, 89.5) | 89.2% (86.6, 91.3) | 78.0% (63.7, 88.0) | 87.6% (84.9, 89.9) |
| wbdH 1006 | 93.5% (84.8, 97.6) | 30.6% (27.2, 34.2) | 93.8% (84.0, 98.0) | 30.2% (26.8, 33.8) | 92.0% (79.9, 97.4) | 29.6% (26.3, 33.1) |
| wbdK 687 | 97.4% (90.1, 99.5) | 92.2% (89.8, 94.0) | 96.9% (88.2, 99.5) | 90.5% (88.0, 92.5) | 96.0% (85.1, 99.3) | 88.7% (86.1, 90.9) |
| wzx 1128 | 97.4% (90.1, 99.5) | 90.4% (87.9, 92.5) | 96.9% (88.2, 99.5) | 88.7% (86.1, 90.9) | 96.0% (85.1, 99.3) | 87.0% (84.3, 89.3) |
| O121 | | | | | | |
| vioA 313 | 77.8% (40.2, 96.1) | 99.7% (98.9, 100.0) | 100.0% (56.1, 100.0) | 99.7% (98.9, 100.0) | 100% (56.1, 100.0) | 99.7% (93.9, 100.0) |
| wbaE 437 | 77.8% (40.2, 96.1) | 98.8% (97.7, 99.4) | 100.0% (56.1, 100.0) | 98.8% (97.7, 99.4) | 100.0% (56.1, 100.0) | 98.8% (97.7, 99.4) |
| wbql 582 | 77.8% (40.2, 96.1) | 99.6% (98.7, 99.9) | 100.0% (56.1, 100.0) | 99.6% (98.8, 99.9) | 100.0% (56.1, 100.0) | 99.6% (98.8, 99.9) |
| O145 | | | | | | |
| wzy 37 | 100.0% (46.3, 100.0) | 98.8% (97.9, 99.5) | 100.0% (46.3, 100.0) | 99.0% (97.9, 99.5) | 100% (39.6, 100.0) | 98.8% (97.7, 99.4) |

[a]All isolates containing stx1, stx2, or both were considered virulent (true positive);
[b]All isolates containing either stx1, stx2, or both and also contained eae were considered virulent;
[c]All isolates containing either stx1, stx2, or both and also contained both eae and hlyA were considered virulent;
[d]sensitivity;
[e]specificity.

The SNP's identified through genetic sequencing of the O-antigen operon in a collection of *E. coli* isolates from each of the six O-serogroups were to a great extent unique to STEC strains. There were several false negatives and false positives for the isolates in our collection associated with the identified STEC SNP's; including 5 false positives for the O26 strains, 2 false positives for the O103 strains, 4 false positives for the O111 strains, and 2 false negatives and 1 false positive for the O121 strains. However, 100% sensitivity or specificity for any SNP would be highly unlikely due to the evolutionary nature of *E. coli* and lateral gene transfer. It is interesting to note that the two O121 isolates in our collection that contain stx1 but do not contain the STEC SNP, do not contain the eae or hly genes. All but one of the false positive isolates (has the STEC allele but does not contain Shiga toxins) in our collection contained the eae gene.

Overall, the sensitivity estimates of the 21 assays were high except for the one targeting the O45 wzy 752 T>C polymorphism (Table 1). The low sensitivity is a result of several STEC O45 isolates that did not have either the STEC or non-STEC allele and were classified as false negatives. The inability for this SNP to accurately differentiate O45 STEC isolates may be due to the discovery of a false SNP because of a sequencing error.

The specificity of the majority of the assays were high, except for two targeting the O26 rmlA 30 G>T polymorphism and the O111 wbdH 1006 G>A polymorphism (Table 1). The results from these two assays showed a large number of non-O111 or non-O26 *E. coli* isolates, as well as *Salmonella* isolates contained the O26 or O111 STEC allele. These assays had low specificity estimates as a result of the large number of false positives. One of the explanations for this large number of false positives may be the close relationship between *E. coli* and *Salmonella*. The SNP's in these two assays may be contained within a region that is highly conserved both between *E. coli* serogroups as well as between *E. coli* and *Salmonella*. Overall, we can have greater confidence in our specificity estimates due to the smaller confidence intervals and large number of samples outside of the selected O-serogroup.

In one embodiment of the invention, amplification of nucleic acids contain the polymorphism of interest. The oligonucleotide primers listed in Table 2 are used to amplify an amplicon fragment containing the nucleotide polymorphism. The probe hybridizes to the DNA amplicon so the next base on the 3' terminal end of the probe is the nucleotide polymorphism. An extension reaction incorporates a nucleotide that represents both alleles of the targeted SNP or doesn't incorporate a nucleotide if the bases isn't one of the two targeted SNPs. The mass of the probe is measured by matrix-assisted laser desorption/ionization-time of flight mass spectroscopy. There are three possible results from the probe mass. First, the mass is equal to just the probe itself meaning there was no extension reaction. Second, the mass is equal to the SNP allele that isn't diagnostic for the assay, and third the mass is equal to the diagnostic SNP allele.

TABLE 2

| Designation | Orientation | Oligonucleotide (5' → 3') |
|---|---|---|
| SEQ ID No: 1 | O26_rmlA_30_Forward | → | ACGTTGGATGCAGGATAAAGACGAGTACCC |

TABLE 2-continued

| | Designation | Orientation | Oligonucleotide (5' → 3') |
|---|---|---|---|
| SEQ ID No: 2 | O26_rmlA_30_Probe | ← | AGTACCCGAACCACC |
| SEQ ID No: 3 | O26_rmlA_30_Reverse | ← | ACGTTGGATGGTGATGGTGGAGCAAGATG |
| SEQ ID No: 4 | O26_wzx_953_Forward | → | ACGTTGGATGTAAAGGGATGAACGCGCTTC |
| SEQ ID No: 5 | O26_wzx_953_Probe | ← | GAGCCTTATATCCCAATATAGTACCC |
| SEQ ID No: 6 | O26_wzx_953_Reverse | ← | ACGTTGGATGCATGGTTTTCATTGTCCTGAG |
| SEQ ID No: 7 | O26_fnl1_88_Forward | → | ACGTTGGATGTCATCCCTGCTAAATATTCG |
| SEQ ID No: 8 | O26_fnl1_88_Probe | ← | CCTGCTAAATATTCGTATTTCAG |
| SEQ ID No: 9 | O26_fnl1_88_Reverse | ← | ACGTTGGATGTGGTGGCACTGGTTCTTTTG |
| SEQ ID No: 10 | O45_rmlB_966_Forward | → | ACGTTGGATGCGTATGTTACTGATCGTCCG |
| SEQ ID No: 11 | O45_rmlB_966_Probe | → | CTCGTCCGGGCCATGACCGTCG |
| SEQ ID No: 12 | O45_rmlB_966_Reverse | ← | ACGTTGGATGTTTCAAAGGTCTCCTGTGGC |
| SEQ ID No: 13 | O45_wbhQ_721_Forward | → | ACGTTGGATGAAAACACCCAGCAGACAGAG |
| SEQ ID No: 14 | O45_wbhQ_721_Probe | ← | GCAGCAGACAGAGTTCTGCGA |
| SEQ ID No: 15 | O45_wbhQ_721_Reverse | ← | ACGTTGGATGCTTTTGATCGCTAATGCGATG |
| SEQ ID No: 16 | O45_wbhU_241_Forward | → | ACGTTGGATGCAACGAGTTTGTCGCTAAAG |
| SEQ ID No: 17 | O45_wbhU_241_Probe | → | ACCAACATTGCGGGAAA |
| SEQ ID No: 18 | O45_wbhU_241_Reverse | ← | ACGTTGGATGGGAATCAGATAAATTCTGGC |
| SEQ ID No: 19 | O45_wbhU_543_Forward | → | ACGTTGGATGTCTTGTTCGTGATGGTGGAG |
| SEQ ID No: 20 | O45_wbhU_543_Probe | ← | TGATAGAACGTCTCATCAAA |
| SEQ ID No: 21 | O45_wbhU_543_Reverse | ← | ACGTTGGATGCGGTATTATCCTGACACGAG |
| SEQ ID No: 22 | O45_wzy_752_Forward | → | ACGTTGGATGCCTGGAAGCTTGTGAATCG |
| SEQ ID No: 23 | O45_wzy_752_Probe | ← | ACCGGAACTATGTGC |
| SEQ ID No: 24 | O45_wzy_752_Reverse | ← | ACGTTGGATGCTATGTTACGGCAGGCCTTG |
| SEQ ID No: 25 | O45_wzy_906_Forward | → | ACGTTGGATGTACCATGGAGCTAGTAGACG |
| SEQ ID No: 26 | O45_wzy_906_Probe | → | GCGACAATGTTTGAAAAGCTAATGCC |
| SEQ ID No: 27 | O45_wzy_906_Reverse | ← | ACGTTGGATGAACCACAATAAGGGAGCCCG |

TABLE 2-continued

| | Designation | Orientation | Oligonucleotide (5' → 3') |
|---|---|---|---|
| SEQ ID No: 28 | O45_wbhW_21_Forward | → | ACGTTGGATGGGCCGTTGTGAAGAAGAGTA |
| SEQ ID No: 29 | O45_wbhW_21_Probe | → | GAAATGAAAGTGTTGTTTTTATG |
| SEQ ID No: 30 | O45_wbhW_21_Reverse | ← | ACGTTGGATGGGTTCGCCTTAATCCATCAG |
| SEQ ID No: 31 | O45_wbhW_997_Forward | → | ACGTTGGATGGCCTTTCATTTTACCACCTC |
| SEQ ID No: 32 | O45_wbhW_997_Probe | ← | TTAGATATCTTTATTTAAACAACATCTT |
| SEQ ID No: 33 | O45_wbhW_997_Reverse | ← | ACGTTGGATGCAAGCTCCTCATCTTCACAG |
| SEQ ID No: 34 | O45_inter_325_Forward | → | ACGTTGGATGATTTACCACTGGAACACGCC |
| SEQ ID No: 35 | O45_inter_325_Probe | → | GAAGTTGGTCTAATCCTGA |
| SEQ ID No: 36 | O45_inter_325_Reverse | ← | ACGTTGGATGTTCTGGGTATCACCATTGGG |
| SEQ ID No: 37 | O45_inter_366_Forward | → | ACGTTGGATGGGAATCAGATAAATTCTGGC |
| SEQ ID No: 38 | O45_inter_366_Probe | → | AGAAATATGCACAAGTGATTTTT |
| SEQ ID No: 39 | O45_inter_366_Reverse | ← | ACGTTGGATGAAAACGTATCCTTCAGGCTC |
| SEQ ID No: 40 | O45_inter_560_Forward | → | ACGTTGGATGTAGTGCAATCCCAATACGCC |
| SEQ ID No: 41 | O45_inter_560_Probe | ← | CATATTTTGCTTTGTGATAATTAC |
| SEQ ID No: 42 | O45_inter_560_Reverse | ← | ACGTTGGATGTAGTGCAATCCCAATACGCC |
| SEQ ID No: 43 | O103_wbtD_937_Forward | → | ACGTTGGATGAAAAAATCAATAACAATAAG |
| SEQ ID No: 44 | O103_wbtD_937_Probe | → | TCAATAACAATAAGAATATTAACCTG |
| SEQ ID No: 45 | O103_wbtD_937_Reverse | ← | ACGTTGGATGTTCATATTTAGCTAACAAG |
| SEQ ID No: 46 | O145_wzy_37_Forward | → | ACGTTGGATGGTCAACACCAGAAAAAATAGC |
| SEQ ID No: 47 | O145_wzy_37_Probe | ← | AACGAAGAAATAATTAACCAAAAAAAA |
| SEQ ID No: 48 | O145_wzy_37_Reverse | ← | ACGTTGGATGAAACGTGAATATAAAGAAAG |
| SEQ ID No: 49 | O111_inter_219_Forward | → | ACGTTGGATGCCAAAGATGTGAGCAGTTCC |
| SEQ ID No: 50 | O111_inter_219_Probe | → | TAGCAGTTCCGCGAGATCC |
| SEQ ID No: 51 | O111_inter_219_Reverse | ← | ACGTTGGATGTTCTGGTCGCATTTGGTAAG |
| SEQ ID No: 52 | O111_wbdH_1006_Forward | → | ACGTTGGATGTAATGTACCTGGGTGTAGGG |
| SEQ ID No: 53 | O111_wbdH_1006_Probe | → | TGTAGGGATATAATAAATGATGGG |

TABLE 2-continued

|   | Designation | Orientation | Oligonucleotide (5' → 3') |
|---|---|---|---|
| SEQ ID No: 54 | O111_wbdH_1006_Reverse | ← | ACGTTGGATGCAAATGGAGGTATCAAAAAGC |
| SEQ ID No: 55 | O111_wbdk_687_Forward | → | ACGTTGGATGGTATTGTTGTGCCTTCGAGC |
| SEQ ID No: 56 | O111_wbdk_687_Probe | → | AAAAGAGAATATGGTTACAGG |
| SEQ ID No: 57 | O111_wbdk_687_Reverse | ← | ACGTTGGATGCGACTCTTCGAAAATATCATC |
| SEQ ID No: 58 | O111_wzx_1128_Forward | → | ACGTTGGATGAAAGGCCATAATGAGCTGCG |
| SEQ ID No: 59 | O111_wzx_1128_Probe | ← | TTAACGTTGAAGCAGCAAG |
| SEQ ID No: 60 | O111_wzx_1128_Reverse | ← | ACGTTGGATGGGTAAATCTAAGCTTGTTGC |
| SEQ ID No: 61 | O121_vioA_313_Forward | → | ACGTTGGATGCTCCTTGGTCTTAAATGGGC |
| SEQ ID No: 62 | O121_vioA_313_Probe | → | CCTGTTTTGTCGATATTGAT |
| SEQ ID No: 63 | O121_vioA_313_Reverse | ← | ACGTTGGATGGCCTCTTCAATTCTTCTCGG |
| SEQ ID No: 64 | O121_wbqE_437_Forward | → | ACGTTGGATGAATGGGTATCAGCAGAGTGG |
| SEQ ID No: 65 | O121_wbqE_437_Probe | → | GCAGAGTGGAACTAATTTTG |
| SEQ ID No: 66 | O121_wbqE_437_Reverse | ← | ACGTTGGATGTTTCAAAGGTCTCCTGTGGC |
| SEQ ID No: 67 | O121_wbqI_582_Forward | → | ACGTTGGATGAGTAGCCTGGAGGCCATTAC |
| SEQ ID No: 68 | O121_wbqI_582_Probe | ← | GAGGCCATTACTACAGT |
| SEQ ID No: 69 | O121_wbqI_582_Reverse | ← | ACGTTGGATGGAGCTGTTTTTACCGACAGA |

TABLE 3

|   | Gene | (5' → 3') |
|---|---|---|
| SEQ ID No: 70 | O26_rmlA Genbank Accession No.: AY763106 | ATGAAAACGCGTAAAGGTATTATTTTAGCTGGTGGTT CGGGTACTCGTCTTTATCCTGTAACTATGGCTGTCAGT AAACAGTTGTTACCGATTTATGATAAACCGATGATCT ATTACCCGTTGTCTACACTGATGTTAGCGGGTCTTCG CGATATTCTGATTATTAGTACGCCACAGGATACTCCT CGTTTTCAACAACTGCTGGGTGACGGGAGCCAGTGGG GCTAAATCTTCAGTACAAAGTGCAACCGAGTCCAG ATGGTCTTGCGCAGGCATTTATCATCGGTGAAGAGTT TATCGGTGGTGATGATTGTGCTTTGGTTCTAGGTGAT AATATCTTTTACGGTCACGATCTGCCGAAGTTAATGG ATGTCGCTGTTAACAAAGAAAGTGGTGCAACGGTATT TGCCTATCACGTTAATGATCCTGAACGCTACGGTGTC GTTGAGTTTGATAAAAACGGTACGGCGATCAGCCTGG AAGAAAAACCGCTACAACCAAAAAGTAATTATGCGG TAACCGGGCTTATTTTTATGATAACTACGTTGTCGA AATGGCGAAAAATCTTAAGCCTTCTGCCCGCGGTGAA CTGGAAATTACCGATATTAACCGTATTTATATGAAC AGGGGCGTTATCCGTTGCCATGATGGGACGTGGTTA TGCATGGCTGGACACGGGGACACATCAAAGTCTTATT GAGGCAAGCAATTTTATCGCAACAATAGAAGAACGT CAGGGGCTGAAAGTTTCCTGCCCGGAAGAAATTGCTT ACCGTAAAGGGTTTATCGATGCTGAGCAGGTGAAAG |

TABLE 3-continued

| | Gene | (5' → 3') |
|---|---|---|
| | | TATTAGCTGAACCGTTGAAGAAAAATGCTTATGGTCA GTATCTGCTGAAAATGATTAAAGGTTATTAA |
| SEQ ID No: 71 | O26_wzx Genbank Accession No.: AY763106 | ATGTTGAAAAAAAAACTTCAAAAAATAAAGGAATAT CATTCAGTATTGGAGTTGGCAATAATTCAGGGTGCGA ATGCCATATTTCCTGTGTTGGTATTCCCATTTTTTCTT ATTACCTTAGGGGAAAACATCTTTTCAAGTATTGCTG TTGGTGAAGTACTAGCACTATATGTGCTTATATTTTCG CTATACAGTTTTGATATTATAAGTGTGCAGAAGGTAA TTTCAAGTGTGACAAAAGATGAAATATTTAAAGTTTA CATTCTGACACTAATCTGTAGGTTGTGTTTATTTGTTA TTTCAGGAATATGTCTTTTATTTATAACGTATTTAATT AATAAAACATTAAGTGTATACTTGGGATTGTTTTTAT TGTACCCAGTAGGGATGATATTGCAATCTAATTATTT TTTCAGGCTACGAATAACAATAGGCCATTGGCTGTT TTTGTACTAATTGCTCGTGGTATGTCATTATGTCTTAT TTATTTTTATAATGGACCAGCAGGCTATTTAACAAGT TATTATTATGTCATTTGTGTGTCTGGTTCGTATTTTT ATCTGGCGTGCTATCGCTTATATATATATATTATCAA AATAAGACTAATAAAGCTAAAATTCAATGGGCGGAA ATTTTAGAATATATGCACAGGTTATCATCTGTTTAT TGCTAATATATTTGTTATTCTATACAGAAATAGTAAT ATTATTATTCTTGGCACTCTTGCTTCGCCTGTTGCAAC GTCTCTGTACGCGACGGCAGAGAAAATTATTAAATGT ATTCAGTCTATAGCAACCCCGTTAAATCAATACTATT TCACGAGGTTGATAAAGCAACATGAATTGAAATTAG AACCATACAAAGTTGGAGAATATAAAAGCCTGCTAT ATGCAAGCACAAATATTCAGCTAAAGTTCATGGTTTT CATTGTCCTGAGTTTAGGGGGGGTGGGTACTATATTG GGATATAAGGTTCAAAGTATCGCTGAAATTAGAAGC GCGTTCATCCCTTTATCAATAATGTCTTTTGCAATATT TATGGGGATATACAATTTTATGTTTGGTTCGGTTGGA TTGTCCATAAGAGGGTATAAAAAAGAATTTTCTTATA TAGTGGCCATTACGGGTGTTTCAACTATTATTTTATCA TTATGCCTGAGTTATTTCTTTGCTGAAATAGGCGCTGC AATTGCTTATGTATTTGCTGAGTTTATCTTACTTATTC TCATACTTAGAATTTATAAAGTGAAACGATTATAA |
| SEQ ID No: 72 | O26_fnl1 Genbank Accession No.: AY763106 | ATGTTTAAGAATAAAACACTCGTTATCACTGGTGGCA CTGGTTCTTTTGGTAATGCCGTACTTAAGCGTTTTCTA GATACAGATATTACTGAAATACGAATATTTAGCAGGG ATGAAAAAAAACAAGATGATATGCGGAAAAAATATA ATAACTCAAAATTAAAATTTTATATAGGTGATGTGCG AGACTATAATTCCGTTCTAAATGCAACGCGTGGTGCC GATTTTCTGTATCATGCAGCAGCCCTTAAACAAGTTC CTTCATGTGAATTTCACCCTATGGAGGCGGTTAAGAC AAATGTTCTGGGTACGAAAATGTTCTGGAGGCTGCT ATTGCGAATGGGATTAAACGCGTGGTGTGCTTGAGTA CCGATAAAGCCGTTTATCCTATCAATGCAATGGGCAT ATCTAAGGCAATGATGGAAAAAGTTATTGTTGCAAA ATCACGTAATCTTGACAGTTCAAAAACAGTTATCTGT GGAACTCGTTATGGAAATGTAATGGCTTCACGTGGAT CGGTCATCCCATTATTTGTTGATCTAATCAAAGCTGG TAAACCATTGACCATAACCGATCCCAATATGACTCGT TTCATGATGACGCTTGAGGATGCTGTCGATCTGGTCC TTTATGCTTTCGAACATGGAAATAATGGTGACATTTT CGTTCAGAAAGCACCTGCGGCAACAATTCAAACATTA GCCATTGCACTTAAGGAATTGCTAAATGCCCATGAGC ATCCAATCAATATTATTGGAACTCGACACGGGGAAA AACTTTACGAAGCGTTATTGAGCCGAGAGGAAATGA TTGCAGCGGAAGATATGGGTGATTATTATCGTGTTCC ACCAGATCTCCGCGATTTGAACTATGGAAAATATGTG GAACATGGTGACCGTCGTATCTCGGAAGTGGAAGATT ATAATTCTCATAATACTGAGAGATTAGATGTTGAGGG AATGAAAGAATTACTGCTAAAACTTCCTTTTATCCGG GCACTTCGTTCTGGTGAAGATTATGAGTTGGATTCAT AA |
| SEQ ID No: 73 | O45_rmlB Genbank Accession No.: AY771223 | ATGCTCAGGTTTCAGAACGCCAGTATCCAGACAAATA CACTAGACGGAACAGATAACGTGAAAATTCTTGTGA CGGGGGGGGCCGGCTTTATCGGCTCAGCGGTTGTACG ACATATTATTAAAAATACCCAGGACGACGTCGTCAAT GTAGATAAGCTGACCTATGCCGGCAACCTTGAGTCGC TGAGTGAAGTCAGCGACAGCGATCGATATGCTTTTGA GCATGCGGATATTTGCGATAAAGATGCTATGGATCGC ATTTTAGCAAAGCATAAGCCTGATGCGGTGATGCATT TGGCGGCTGAAAGTCATGTCGATCGTTCTATTACCGG CCCGGCGGCTTTTATCGAAACCAATATCGTTGGCACT |

TABLE 3-continued

| Gene | (5' → 3') |
|---|---|
| | TATGTGCTTCTGGAAGCCGCCCGGGCTTACTGGTCAA<br>CGTTGGATGAGCAAGCGAAGAAAGCGTTCCGTTTTCA<br>TCACATTTCTACCGACGAAGTGTATGGTGATTTGCCG<br>CATCCTGATGAACATCCCGCATCAACTGAGCTGTCAC<br>TCTTCACTGAAACCACCGCATATGCACCTAGCAGCCC<br>ATATTCAGCGTCGAAAGCCTCGAGCGACCATCTCGTT<br>CGTGCCTGGTTGCGCACCTATGGTTTCCCGACCATTG<br>TCACCAACTGTTCAAATAACTATGGCCCGTATCATTT<br>CCCTGAAAAACTGATCCCTCTGGTTATTCTGAATGCG<br>CTGGACGGTAAAGTTTTGCCTATTTACGGCAAGGGGG<br>ACCAGATTCGTGACTGGCTGTACGTTGAAGACCACGC<br>CCGCGCACTCTACACCGTTGTCACTCAGGGGAAACCG<br>GGTGAAACGTACAATATTGGCGGTCATAACGAAAAG<br>CAGAACTTGGATGTGGTCCATACGATTTGCGATCTGC<br>TTGATGAGATTGTGCCAAAAGAGGGATCTTATCGCGA<br>TCAGATAACGTATGTTACTGATCGTCCGGGCCATGAC<br>CGTCGCTACGCCATTGATGCAAATAAAATTAGTGCTG<br>AGTTGGGATGGACGCCACAGGAGACCTTTGAAAGTG<br>GTATTCGTAAAACCGTTGAATGGTATTTGACAAATAC<br>AGAATGGGTGGAAAACGTTAAAAGCGGTAATTATAA<br>ATCCTGGATTGCGCAAAATTATCAAATCGTTAA |
| SEQ ID No: 74 | 045_wbhQ<br>Genbank<br>Accession<br>No.:<br>AY771223 | ATGTTATATCTGGGCATTGTCGTTTTTGCATTCTTTAT<br>ATCATGCGCGTTGACTTGGGGTTTAAGGTTATATGCC<br>ATCAAGAATAATGTAATTGATCAACCAAACCAAAGA<br>AGTTCTCACAGTGTTCCTACGCCTCGTGGGGAGGGG<br>TGGCTATTGTATTAACATTGTTGGCTTCATTAATATGG<br>CTGGTCCTTACAAATCATATAACTCAGGCAACATTTT<br>TAGGTTTCTTCGTGACTGGCTTATTGATTGCGGTTATT<br>GGTTTCCTCGACGATCATGGCCATATCGCTGCACGCT<br>GGCGCTTGTTAATGCATTTCATCGCTGCAGCTATAGG<br>GCTTTTTTATCTAGGATCTTTCCCAAGCATTAATATGT<br>TTGGCTACGATGTTTCTTTGTCATGGTTTGGAATGATC<br>CTCGGTAGTATCTATCTTGTATGGATGTTGAATTTATA<br>TAACTTTATGGATGGTATTAATGGTCTTGCAAGTGCG<br>CAAGCTATTACCTTTTCGCTTTGTAGTATCTTGATAAT<br>AACTATCAATAACTACTCTGATTCATCTGATGCAATG<br>ACTATGCTTGCATTAGCACTCGCTGGATCGGTCGCGG<br>GATTCATCGTGTGGAACTTCCCTGTGGCAAGGATCTT<br>CATGGGCGATGCTGGAAGCGGTTTTCTGGGTATCACC<br>ATTGGGCTGATGATCCTTTATTTTGCAAAGCTAGACT<br>CACGTGTTCTGATCGCAGAACTCTGTCTGCTGGGTGT<br>TTTCATTGTTGATGCAACTACTACCTTACTGAGAAGA<br>TTACTGGCGGGTAAGAAAGTCTATGAAGCACATGCA<br>AGTCATTGTTACCAAATTCTTGCCCGTAAATATAAGA<br>GCCATGTTCCTGTTACTATGGCGGCTATAGCTATTAA<br>CTTCATGTGGCTGCTCCCTATTGCTTACTTAATCATCT<br>CTGCAAAAATTGATGGAATTGTAGGCATTACCATCGC<br>TTGGTTACCATTGATGATTCTTGCATTCAGATGTGGTG<br>CTGGAGTTAAAGATAAAGAGAGGGCATAA |
| SEQ ID No: 75 | 045_wbhU<br>Genbank<br>Accession<br>No.:<br>AY771223 | TTGGTGCAGTACAATGATAAGATTTCAATAGTGGTCC<br>CTGCCTATTGTGAACCATCGAAAGTTAAGCGTTTCAT<br>GGATGCCATACTGAATATTGATTATCCAGATAACCTT<br>ATTGAATTAATTCTTATTGACGATTGTAGTCCGGTTTC<br>ACTGGAAGAAATCGCAGCCTCTTATGGAGAAGTCTTT<br>AAAGATAAAATAAATTTTTTATTCCACAGGAATCAGA<br>TAAATTCTGGCAGGGCTATTTCCCGCAATGTTGGTAT<br>TTCTTTAGCGACAAACTCGTTGATAATGTTTATTGATA<br>TCGATAACCTGCTTGAACCTTATGCAATAAAAAAAAT<br>TGTTTCTTTTTTCCATGGTAAGCACTTCACTGCAGCCA<br>GAATTAATATACGAATCGACCCTGCCAGACTTTCCAC<br>TAGCAATTATCTCCGTTATTTTGATAGCCGTTATCTCG<br>GAGCGCGTAATATCCCTGAAGGGATCATAAGTACTCG<br>TTTCTTTGCAAGTGACGGTATTATCCTGACACGAGAC<br>ATCATTAATACAATCGGTGGTTTTGATGAGACGTTCT<br>ATCATTACGGCTGTGAAGATGAGGAGCTTGGAATCCG<br>AGTTTCAAAAGCGAAATATGACTTTTATTTTTTACCC<br>AATGCAAAGGCAGAAGACAGTGATACACCAACATTG<br>CGCCGAGCATCAGAAAGAATGGTTGTGTATGCATCA<br>AAATCTTTCCCTGTATTGAAAGAAAAACACCCGGAGT<br>GCGTGAAGGATAGTCTCTTTTCATCCTACGAGGTAAT<br>GTTAGATGATACGAGACTCCGCAGTAAATTACTCATA<br>AATGTTATTCATCTTCTTCCTCTTACAACAACCCGCAA<br>AAGCCTTCTTTGGTTGTGTGATAAATTAGATGCAAAA<br>GCGATTAAAGTTCCTGACTTCATATATAAGTTCGTAT<br>TGGCACTTTCATATATTGAAGGTGGAAAACTTCGGTA<br>G |

TABLE 3-continued

| | Gene | (5' → 3') |
|---|---|---|
| SEQ ID No: 76 | O45_wzy Genbank Accession No.: AY771223 | ATGAGTATTTTTTTAATGTCCCCAGGGTTTGTGTATGC TTCAATTTGGCTGTTCACAATTATATTATATTCGCTTG GAGTGACTACTAATATTAGCCCGCTCTCAAATGAGAT GGTGGTGTTTTATCAATTAATGTTACTCTGGGTTTGA TTTTTTCACTTCCATTTATTACTCCTGGCAGTATTAAT CGCGTTCGTCTGGATGAAATTATGCCATCTTGGCGAG CGACTAAAATATGGCTCATCATTTGGTGCTTTGTGAT AATTCCTGATGTGGTTGCTGCTGGCGGGATACCAATG ATTATGCAATTAGGGGCGGCTATAATTATACCGAGT TCGGTATACCGACATATCATGGGATAGTTAATATGCT ATTCCTTTTTGTTTTTCCGTCACTGTATTATCATTTTCT TTTATCAAAAAGAAAAATTATTCTGCTGATTATACTA TTGATGAGTATATGGGAAATGCTGGTCTTCAGACGAG GTATACTGATGTCAGGCCTCGTGGAAATATTCTTTTT ATTTTTTATCTATAAAAAATTCACTAAAAAGATGTTT ATTTATACAGTATTTTCTGTAATCACAATAGTTCTACT TTTTGGAGCTGTAGGAGATATCAGGGGCGCTGAAAAT CCTTATCAATATTTGTTGTCACCAGAAGGACAATTTC TGTCGAGTTTGCCTTCAGGCTTCACATGGTTTTATGTC TATGTTACGGCAGGCCTTGCAAACCTTGCATATAACT TTGCGCACATAGTTCCGGTATACGATTTCACAAGCTT CCAGGACCTATTCCCCAGTGTTATCAGAAATCTCATT TACAGTGATTTAGGATTCCATGATACCATGGAGCTAG TAGACGATAATGCCAACGTTTCGACAATGTTTGAAAA GCTAATGCCCGATCTTGGGATCGCGGGCTCCCTTATT GTGGTTACATGTTTACTTCTGCTTTTTAGTATTGCTTA CAAGAATTTGCTTAAATCGTATCATTATAGTTTATTTC CTTATGCGATTGCAATGCAATGTGCAATATTCAGTGG CTTTTATAATTTATTCTTTATTCAAACATATTTTTACT TTTCATTGTTACTCTTGTTTTTGTGAGAATTAAAATAT TTACAGGGAGCCATTCTCATGTTTGA |
| SEQ ID No: 77 | O45_wbhW Genbank Accession No.: AY771223 | ATGAAAGTGTTGTTTTATGTCCTCGTTTTTTAACTA TGAAAATGAAATATCTGATGGATTAAGGCGAACCGG TGCCACCGTTGATTATTTCGATGAGAAACCATTTAAT AACGTATTTTTTAAAATATTACTCAGACTTTGGAAAG GTAATAATTTTATTAAACGTATTTCAGACGCGTATTTT GAGAAGATTTTGCTTCAAACAAATGATGACTATGATT ACGTCATAGTACTCAAAGGTGAATCTCTTGATAGAAA AAATTTATTGAAATTCAAAAATAAATATAAGAACGCT AAATTCATTTATTACGCATGGGATTCTATTAAAAACT ACCCTCATATTCAAGAGTGCCTGAATTTATTTGACCG CGTATTTACCTTTGATGATAACGATGCGCGAGAATAT GATTTTATGACTCATTTGCCATTGTTTTATTCCCCGGA TTTTGTAAGCACAGCGAAAAAAGAAGCTTCAAAGAA TTTTAAGCCATCTATTGCATTTCTCGGTACCGTACATA GTGACAGATACAGAGTATTGGGAGAGGTTTATGAGA AATATAAAAATGAATATGATTTGAGGTTTGTTCTTTA TTTCCCTTCAATTGTTGTCTTGGTAGGTTTTCTTCTTAC TAATTTTAAGTCAATCATTAGGTTCAAACTTTTTAGTT TTACCCTTCGCTCTAGAAGTAAAAAGCAGATAGCATC ATTCTTCTAGTGCTGATGCGGTCCTTGATATCCAGC ATCCCCGTCAGACAGGTTTGACGATGAGGACAATAG AATGCTTGCCTCTCAAGAGGAAATTTATAACTACCAA TTCACGAGTTAAAAATTACGATTTTTATTCCGCTGAA AATTTTTACTTTATCGATCGAGATAATATCCTTATCGA CTCTGATTTTTCGAAATCCCATATAACGATGCGCAC CTAGATGCAATTTCGCGTTATAGTATAGACTCGTGGG TAAAAACATTATGTTCGACTCATATCAGAGAAGATGT TGTTTAA |
| SEQ ID No: 78 | O45_inter- genic_region_ downstream_ from_rmlA Genbank Accession No.: AY771223 | TAGTTATTGTTATCTAACAATATCATATCTTTCATGGG GATCTAGTAATAATTCTAAAATGAAAGCAAAATATTT TTTCTTTACCTCTGTACTTCTGTTTACCTTCTGCGTTCTC CGCGAAAAACAGCAATGCAATTTTCTCTTAGGCACGG TATCATCATCCTACTAAGTTGAAGGTGGTTGGAATAA AAATGGAAAGGGGCCTTCAGATTGGGATTATTTTACC CATAATGAGGTCACAAAATATACCATTGGCACTGTTG GAAATTTACCACTGGAACACGCCATTAGCACTTTATA AAAAAGGAAGTTGGTCTAATCCTGAATCACCAGTTTG GTTTGAGAAATATGCACAAGTGATTTTTGAAAATTTT GGTAGCAGAAGTTATTATTTTCTAACTTTTAATGAGC CTGAAGGATACGTTTTACTCAGGAACCTCTTGCAGC AAACCTTATTGATAAAAAGCTAGACGGATATCGTGAT GTTTTATCCGTTGTTTCTCGTGGAAAATAAGCGATAG CATTTCACAATCTTTTGATCGCTAATGCGATGGTTGTA CGTAATTATCACAAAGCAAAATATGATGGACGTATTG |

TABLE 3-continued

| Gene | (5' → 3') |
|---|---|
| | GCGTATTGGGATTGCACTAAACTTATCGCCAAGCATT |
| | GATAATGACCAACCAAATAGTGCTACTGAGAAGTTAT |
| | GAAACGATATTCATAACAACTAGATTCTGGATGTTAT |
| | TTATAAGAGGGAATACCCTCATTCAGTATTGAAAATG |
| | TATTAGTCTACATATCCTAAATTCAAGCCTACATTTCA |
| | AGATATGCAATTCATTACCTAGGGAAAACCTGATTTT |
| | ATCGGCGTAAATTGTTATGGTCCAACATTGGTTAAGT |
| | ATGATAAATCTGAACCGTTTGAAATATGTAACGTTTC |
| | AAATCCAGATAAAGGGCCTTCTGTCAACGGTCCATTC |
| | TCTCCAGAGGCGCTGGTAATGATGATGAAAAAGTTTG |
| | ATATACAATATTCGCATCCTACCTTCATTATTACTGAG |
| | TATGGTGCAGGTTTTGGTTTAGCCGATAAAAAATTTA |
| | ATGATGGCATTATTTCTGATAAGTTGCGAGTAGACTA |
| | TCTCAAGAGATATGTATCTGCAGTTATTGAAGCAAAA |
| | AAGAAGGTTTAGATATCCATGGCTATCTATTTTGGAG |
| | CTTGCTTGATAATTTCGAATAGTTATAGGGTTACAAA |
| | AATAGGTTTGGCATAATTGGTGTTGATTTTAATGATA |
| | AGGCTTTGAAGCGAACACCGGAGTTAAGCTATTATAG |
| | CTACCAGAAAATTATTAAAGAAAATAAAAATCAATG |
| | TGTTTTATTGATGAGAAAATAATCCACAATAAACCAT |
| | GTCTTTTGTTAAGGCTTAAGTGTGTCAATGACCATAA |
| | TTACCTACCTCTGCTCTCGATTTCTGAGTTAAGATAAT |
| | TCGATAATATATCCACCGGGAAGTACCCCGGTGGGA |
| | GCACACCTGACAGGAGTATGTAATGTCAAAGCAACA |
| | GATCGGCGTCGTCGGTATGGCAGTG |
| SEQ ID No: 79 O103_wbtD Genbank Accession No.: AY532664 | ATGATAATATCTTCAGATAACCTAAGTGTTATTATCC CAGTTTATAATGAAGAAGAATGTTATTAATATTCT TCAATCTCTTGAATGCCAGTCTTTAACGGGATTTAAT GTTATTGTCATTGATGATGGTTCAAAAGATATGACTG CTTCTCTTGTAAAAGAATATAAACCATCATCATATAG TTTAAGCTTAATACAACAAAGTAATATGGGGCTGCT CGGGCAAGGGAGAATGCCATCAATTTTACTCATAGTG AGTATATTGCATTTATAGATAGTGATGACTCTTTAAG TTCAGATGCTCTTGAAAAAGCATTAGCTCCGATGCTG GATAATAAAGATATCGACATCTCACTATTTGAACTGG TACATATTAAAAACTTAAATCATGATACTAATAACAT ATTTGTACCTTATTCTACAACCAAATTAATATGTGGA GAAGAGGCTTTTGCTAATTGTATTTCATATTGGGGAT TGCATGGGTTTGGTATCTACAAAAGAAAATTGATTCA AAAATCCTATGGTATTTATTATAAATATAATAAAAAC AAAGAAAATTATATAAATAATGATGAGGTTATTTCAA GAATCAGTTTTGGATTATCTAAAAATATCTATTTATC ATCTGGAAGATATTTCTTTGTACAGAACATGGATTCA ACAACAAGAAGAATAAATGAAAGTTATTATAAAGTT ATAAATAATGCTGTTTATTTAAGAGAGTATATAGATG AAGAAATAAAATATAATGATTTTGATTGTCTAGGTGA AGCTAATAAACTCCTTGTAAGTACTATATGGGGAGTG TTTGTTCGTTATCAAAAATGGAAGAAAAAATTCAGTG ATGAAACAAACGGTAAATGGCGCGAAGCAATAAAAA AAGGAATGCAATATATAAAAAAAATCAATAACAATA AGAATATTAACCTGCATATTAAATCTAAAATGCAATT ATATATAATATCTAAACTTGTTAGCTAA |
| SEQ ID No: 80 O145_wzy Genbank Accession No.: AY863412 | GTGAATATAAAGAAAGATAAGTTTATAAATGGAGTG CTTTTTTTTTGGTTAATTATTTCTTCGTTATATTACTTA AATGCTATTTTTTCTGGTGTTGACACATTAAAATATA ATGAAGATTTAACGCAAAAAATTATAAAATATATAGT TTGCTTAGTTATAAGTCTAAGTATCTTATTTATTTACA AGAAATTTAATTATTTTTTGTATTGTTTTTTTCTTGT TCCTGTCTGTTGCTTCAGCCCTTTTCAGTGGTGCGGTA ACAATTTACGCAACAACAATGTTGATTATTGCAACTA TGATCAGCTTTTGCCTGATTATTCCTCTATTTTCTTAT AATATGGTGAAAGTTAATAGAGTTCTTTTATGGACAG GAGTTATTGTAGGCACGATTTCTGTATTAGAATTAAC GGTATTTTATAATTATATGGTTTCATATTGGGCTGCCA CTGATGGGATTAGGTCAATATCTTCTCTTCTGAATCCT ACGAATAGTGGTGCTTATTCAGCGATTATTATTTTAA TCGCCTTGGTGACAAATATAAAAAGTCTTTTTAAAAG AGCTTTATTTCTTATAATGCCGATGATAACGTTAATTA GCAGTGGTTCGCGCACAGCATGGTTATCACTTGGTAT GACACTTTTATTAACAGTAGTATTGAGAGACAGTGCC AGCATTCGCTTGCGAAAAAAAAATATTTCTTGCAA GCATTGGCACTGTTTGCGGTGCATTGTACGCCATATT TTATATGGGCAGTATCTCTGGTATTGAATCACAATAT CGAGGTCTTAATACGTATACTGCATCAATTCGAGTTG AAAACTTTCTGCACATATTTAAATTTAGTTGATCTGAA TATGTTGCTACCTGATTTTTTAGATAAAAATATAAAT |

TABLE 3-continued

| | Gene | (5' → 3') |
|---|---|---|
| | | CTCATTTCAGATAACTTTTATCTCGTAATGTTTAATTA<br>TGCCGGTCTAATCGGCTTTTTTATTGTTTTATTAATTT<br>TATTGCTGCTTATCTTCTGGAACATACAATTTAAAAT<br>ATTTAATGAGTTAATGGCTGAAGATATAGCCATTTGG<br>AGAGTTGTTTTTATTTATTTCCTAATATCCGGGCTTTC<br>AAATTCATTTATAAATTCTTTTCCTGTAAATCAATTGT<br>TCTTTATCTCATGCGGATATTATATATATAAATATAA<br>ATTAGTTAAAAGCTCTATAGGAAGATAA |
| SEQ ID<br>No: 81 | O111_inter-<br>genic_region_<br>between_galF_<br>and_wbdH<br>Genbank<br>Accession<br>No.:<br>AF078736 | AGATTTACACGTCTTTGTGACGATAAGCCAGAAAAAA<br>TAGCGGCAGTTAACATCCAGGCTTCTATGCTTTAAGC<br>AATGGAATGTTACTGCCGTTTTTTATGAAAAATGACC<br>AATAATAACAAGTTAACCTACCAAGTTTAATCTGCTT<br>TTTGTTGGATTTTTTCTTGTTTCTGGTCGCATTTGGTA<br>AGACAATTAGCGTGAGTTTTAGAGAGTTTTGCGGGAT<br>CTCGCGGAACTGCTCACATCTTTGGCATTTAGTTAGT<br>GCACTGGTAGCTGTTAAGCCAGGGGCGGTAGCTTGCC<br>TAATTAATTTTTAACGTATACATTTATTCTTGCCGCTT<br>ATAGCAAATAAAGTCAATCGGATTAAACTTCTTTTCC<br>ATTAGGTAAAAGAGTGTTTGTAGTCGCTCAGGGAAAT<br>TGGTTTTGGTAGTAGTACTTTTCAAATTATCCATTTTC<br>CGATTTAGATGGCAGTTG |
| SEQ ID<br>No: 82 | O111_wbdH<br>Genbank<br>Accession<br>No.:<br>AF078736 | ATGTTACTATGCTGCATACATATCAATGTATATTATTT<br>ACTTTTAGAATGTGATATGAAAAAAATAGTGATCATA<br>GGCAATGTAGCGTCAATGATGTTAAGGTTCAGGAAA<br>GAATTAATCATGAATTTAGTGAGGCAAGGTGATAATG<br>TATATTGTCTAGCAAATGATTTTTCCACTGAAGATCTT<br>AAAGTACTTTCGTCATGGGGCGTTAAGGGGGTTAAAT<br>TCTCTCTTAACTCAAAGGGTATTAATCCTTTTAAGGAT<br>ATAATTGCTGTTTATGAACTAAAAAAAATTCTTAAGG<br>ATATTTCCCCAGATATTGTATTTTCATATTTTGTAAAG<br>CCAGTAATATTTGGAACTATTGCTTCAAAGTTGTCAA<br>AAGTGCCAAGGATTGTTGGAATGATTGAAGGTCTAG<br>GTAATGCCTTCACTTATTATAAGGGAAAGCAGACCAC<br>AAAAACTAAAATGATAAAGTGGATACAAATTCTTTTA<br>TATAAGTTAGCATTACCGATGCTTGATGATTTGATTCT<br>ATTAAATCATGATGATAAAAAAGATTTAATCGATCAG<br>TATAATATTAAAGCTAAGGTAACAGTGTTAGGTGGGA<br>TTGGATTGGATCTTAATGAGTTTTCATATAAAGAGCC<br>ACCGAAAGAGAAAATTACCTTTATTTTTATAGCAAGG<br>TTATTAAGAGAGAAAGGGTATATTTGAGTTTATTGAAG<br>CCGCAAAGTTCGTTAAGACAACTTATCCAAGTTCTGA<br>ATTTGTAATTTTAGGAGGTTTTGAGAGTAATAATCCT<br>TTCTCATTACAAAAAAATGAAATTGAATCGCTAAGAA<br>AAGAACATGATCTTATTTATCCTGGTCATGTGGAAAA<br>TGTTCAAGATTGGTTAGAGAAAAGTTCTGTTTTTGTTT<br>TACCTACATCATATCGAGAAGGCGTACCAAGGGTGAT<br>CCAAGAAGCTATGGCTATTGGTAGACCTGTAATAACA<br>ACTAATGTACCTGGGTGTAGGGATATAATAAATGATG<br>GGGTCAATGGCTTTTTGATACCTCCATTTGAAATTAA<br>TTTACTGGCAGAAAAAATGAAATATTTTATTGAGAAT<br>AAAGATAAAGTACTCGAAATGGGGCTTGCTGGAAGG<br>AAGTTTGCAGAAAAAAACTTTGATGCTTTTGAAAAAA<br>ATAATAGACTAGCATCAATAATAAAATCAAATAATG<br>ATTTTTGA |
| SEQ ID<br>No: 83 | O111_wbdK<br>Genbank<br>Accession<br>No.:<br>AF078736 | ATGATTACATACCCACTTGCTAGTAATACTTGGGATG<br>AATATGAGTATGCAGCAATACAGTCAGTAATTGACTC<br>AAAAATGTTTACCATGGGTAAAAAGGTTGAGTTATAT<br>GAGAAAAATTTTGCTGATTTGTTTGGTAGCAAATATG<br>CCGTAATGGTTAGCTCTGGTTCTACACGCTAATCTGTT<br>AATGATTGCTGCCCTTTTCTTCACTAATAAACCAAAA<br>CTTAAAAGAGGTGATGAAATAATAGTACCTGCAGTGT<br>CATGGTCTACGACATATTACCCTCTGCAACAGTATGG<br>CTTAAAGGTGAAGTTTGTCGATATCAATAAAGAAACT<br>TTAAATATTGATATCGATAGTTTGAAAAATGCTATTT<br>CAGATAAAACAAAAGCAATATTGACAGTAAATTTATT<br>AGGTAATCCTAATGATTTTGCAAAAATAAATGAGATA<br>ATAAATAATAGGGATATTATCTTACTAGAAGATAACT<br>GTGAGTCGATGGGCGCGGTCTTTCAAAATAAGCAGG<br>CAGGCACATTCGGAGTTATGGGTACCTTTAGTTCTTTT<br>TACTCTCATCATATAGCTACAATGGAAGGGGGCTAGT<br>TAGTTACTGATGATGAAGAGCTGTATCATGTATTGTT<br>GTGCCTTCGAGCTCATGGTTGGACAAGAAATTTACCA<br>AAAGAGAATATGGTTACAGGCACTAAGAGTGATGAT<br>ATTTTCGAAGAGTCGTTTAAGTTTGTTTTACCAGGAT<br>ACAATGTTCGCCCCACTTGAAATGAGTGGTGCTATTGG |

TABLE 3-continued

| | Gene | (5' → 3') |
|---|---|---|
| | | GATAGAGCAACTTAAAAAGTTACCAGGTTTTATATCC ACCAGACGTTCCAATGCACAATATTTTGTAGATAAAT TTAAAGATCATCCATTCCTTGATATACAAAAAGAAGT TGGTGAAAGTAGCTGGTTTGGTTTTTCCTTCGTTATAA AGGAGGGAGCTGCTATTGAGAGGAAGAGTTTAGTAA ATAATCTGATCTCAGCAGGCATTGAATGCCGACCAAT TGTTACTGGGAATTTTCTCAAAAATGAACGTGTTTTG AGTTATTTTGATTACTCTGTACATGATACGGTAGCAA ATGCCGAATATATAGATAAGAATGGTTTTTTTGTCGG AAACCACCAGATACCTTTGTTTAATGAAATAGATTAT CTACGAAAAGTATTAAAATAA |
| SEQ ID No: 84 | O111_wzx Genbank Accession No.: AF078736 | ATGGTATTAACAGTGAAAAAATTTTAGCGTTTGGCT ATTCTAAAGTACTACCACCGGTTATTGAACAGTTTGT CAATCCAATTTGCATCTTCATTATCACACCACTAATA CTCAACCACCTGGGTAAGCAAAGCTATGGTAATTGGA TTTTATTAATTACTATTGTATCTTTTTCTCAGTTAATAT GTGGAGGATGTTCCGCATGGATTGCAAAAATCATTGC AGAACAGAGAATTCTTAGTGATTTATCAAAAAAAAA TGCTTTACGTCAAATTTCCTATAATTTTTCAATTGTTA TTATCGCATTTGCGGTATTGATTTCTTTTCTTATATTA AGTATTTGTTTCTTCGATGTTGCGAGGAATAATTCTTC ATTCTTATTCGCGATTATTATTTGTGGTTTTTTCAGG AAGTTGATAATTTATTTAGTGGTGCGCTAAAAGGTTT TGAAAAATTTAATGTATCATGTTTTTTTGAAGTAATTA CAAGAGTGCTCTGGGCTTCTATAGTAATATATGGCAT TTACGGAAATGCACTCTTATATTTTACATGTTTAGCCT TTACCATTAAAGGTATGCTAAAATATATTCTTGTATG TCTGAATATTACCGGTTGTTTCATCAATCCTAATTTTA ATAGAGTTGGGATTGTTAATTTGTTAAATGAGTCAAA ATGGATGTTTCTTCAATTAACTGGTGGCGTCTCACTTA GTTTGTTTGATAGGCTCGTAATACCATTGATTTTATCT GTCAGTAAACTGGCTTCTTATGTCCCTTGCCTTCAACT AGCTCAATTGATGTTCACTCTTTCTGCGTCTGCAAATC AAATATTACTACCAATGTTTGCTAGAATGAAAGCATC TAACACATTTCCCTCTAATTGTTTTTTTAAAATTCTGC TTGTATCACTAATTTCTGTTTTGCCTTGTCTTGCGTTA TTCTTTTTTGGTCGTGATATATTATCAATATGGATAAA CCCTACATTTGCAACTGAAAATTATAAATTAATGCAA ATTTTAGCTATAAGTTACATTTTATTGTCAATGATGAC ATCTTTTCATTTCTTGTTATTAGGAATTGGTAAATCTA AGCTTGTTGCAAATTTAAATCTGGTTGCAGGGCTCGC ACTTGCTGCTTCAACGTTAATCGCAGCTCATTATGGC CTTTATGCAATATCTATGGTAAAAATAATATATCCGG CTTTTCAATTTATTACCTTTATGTAGCTTTTGTCTATT TTAATAGAGCGAAAAATGTCTATTGA |
| SEQ ID No: 85 | O121_vioA Genbank Accession No.: AY208937 | ATGGAAAAGCCAATCTTTGTAACGCAACCTAATTTAC CACCGCTAGAGGAGTTTATACCATATCTGGAAATCAT TTGGCAGAATAAGCAATTTACAAATAATGGTCCAATG CATCAAAAATTAGAAAAAAAATTATGCGAGTTTCTTG GTGTTGAATACATTAGTCTATTTAATAATGGGACTAT TGCGCTTATAACCGCAGTACAGGCTTTGGGTGTTAAA GGCGAAGTAATTACCACACCATATTCCTTTGTAGCAA CTGCACACTCCTTGGTCTTAAATGGGCTTAAACCTGT TTTTGTCGATATTGATTCCAAAACCTTAAATATCGATC CGAGAAGAATTGAAGAGGCGATTACCCCTGAAACGC AGGCAATAATGCCGGTGCACTGCTATGGGAATCCTTG CGATACACAAGCTATTGCTGATATTGCGCAAAAATAT AATTTAAAGGTCATTTATGATGCTGCGCATGCCTTTG GCGTTGAAGATGATGATGGAAGTGTTCTTCGCCATGG AGATCTAAGTGTCTTAAGTTTCCATGCAACTAAAGTG TTCAGCACTTTTGAAGGCGGAGCTATTGTGTGTAATA GTAAAGAAATGAAAGAAAAAATTGATAGACTAAAAA ACTTTGGTTATATCGATGAAACTAACATCAATATCAT TGGCTCTAATGGAAAAATGAGCGAAGTTAATGCTGCT TTCGGCTTGCTACAATTAGAACATATGGATACTTTTCT ACGTGGTCGAATGAATGCTGACATGTTTTATCGGCAG AAACTTAAAGATATCACTGGTATAAGCATAGTAATTC CCAGCGGCCAGAAAATATCGAATTTTTCATATTTCCC TATATTGGTTGAATCTGATTTTCCGTTATCTCGTGATG AACTATTTAATTATCTGAAGAACCAGAATATTTTTGC AAGACGTTATTTTTATCCTGTTATACCAGATTTTTGC CGTATTTGAATGTAGGTGAAGTCTGTGATGTCAAGAA TGCCCGTGAAATAGCCTCGAAAGTGCTTTGCCTACCG ATGCATGCAGAATTGAGCTCTGATATCTTAGAATATA TTGTAAGTACGATTAGGGAGATTAAATGA |

TABLE 3-continued

| | Gene | (5' → 3') |
|---|---|---|
| SEQ ID No: 86 | O121_wbqE Genbank Accession No.: AY208937 | ATGGAAGGAACAGTTCCTAAGGTCTCAGTCTGTGTGA<br>TAACATATAACCAGGCGAAATATATAAAGCAATGCA<br>TAGAAAGCCTAATCACTCAGGACTGTGATTTCGATTA<br>TGAAATAATTGTGAGCGATGATTGTTCGACGGATAAT<br>ACACGAGAAATTTTAGAACACTTATATCATCAATATC<br>CAGAAAAGATACGTATATTTATACATGAAAAGAATCT<br>TGGGGTTACTAAAAATTATCTTTTCCTGCATGAACAG<br>GCGCAAGGCGAGTATATTGCACATGTTGATGGTGATG<br>ACTACTATTTTTCAAATAAATTAAGTTTACAAGCACG<br>ATATCTTGATGAAAATAAAGAGTGTAATATTGTTTGG<br>CATCCTATGTTGTTAGATAATAATTCACGAGTATTTA<br>ATGGGTATCAGCAGAGTGGAACTAATTTTGTCGATTT<br>AAAATTTACTCAAGGTGACATAATTCAATATATTTCT<br>GTCGGTAAAAACAGCTCAAAGATGTATCGAAAAACC<br>GTACGAGATATTGATATACCTGCATTCGAGCTCGTTG<br>ACTACCTCGTTAATGTTGAACAAGTTCAGAATGGCTA<br>TGGTGGATATGCTTCGAATGAACCTCTGGGAGTATAT<br>CGAGTAGGTGTAGGAATTTCATCTTCTGGAGACAAAA<br>CTCGCATTGCTCTTCGGGATACTTTTCTTTATCTATTA<br>AAAAAGTATCCAAAATACAGATTAGAAATAAATACA<br>GCGGCCTTGACATATTTTATCCGCGATATCTTTGCAA<br>GAAGAAAATCTGCAAAGATTTTTTTACATGTATGGAT<br>AAAAACGTTTCATCCCTTTTCAGTAATTAAATTACTTA<br>AGGGGATGAGTACAATTAAAAAATTAAAATATAGAG<br>CATAA |
| SEQ ID No: 87 | O121_wbqI Genbank Accession No.: AY208937 | ATGAAAAAGATTGTTTTTATAATCAATAATGTCGATT<br>TTTTAATATCTCATCGATTACCTATCTTACTCGAGGCT<br>CAGAAAAATGGGTTTCAGGTTCATGTGATTGCTCCTA<br>ATTCCAGGAATAATGAGCTACTAAAGAAGCATAAAA<br>TAATGGGTCATGATCTCTTTCTTTCCAGAGGAGGTAA<br>TAACCCTTTTTATGATTTATTTACTTTGCTTCAGCTTA<br>CAAAAATTCTGAAATTTCTCAAGCCCGACCTTGTCCA<br>TCTTGTCACGATTAAACCAACACTTTATGGTGGGATT<br>GCTGCCAGAATCGCCAAAGTGCCTCATGTCGTTGCAG<br>CTGTCTCTGGGCTGGGAACCGTATTCTTGAGCAGAGG<br>AATCATCAGTGGCTTACGTCGCTTACTGGTTACAACC<br>TTGTATCACTCCGCTCTGAAACATAAAAGAATACGCG<br>TTATCTTTCAGAACCCTGATGATCGTGAGTTACTTGTG<br>AGCGCAGGCATATTAAAGGTTTCCAATTCCTGTCTGA<br>TCAGAGGTTCGGGGGTTGATTTAAGAGAGTATCCTTA<br>TCTTCCTGAAAAAGTTCACGGTAAAACTGTAGTAATG<br>GCCTCCAGGCTACTAAGGGATAAAGGGGTTTATGAGT<br>TTATCGAAGCCGCTCGCTTACTTAAACAAAGGAATGT<br>AGAGGCTGATATTAGAATCATTGGTTCTCCAGATACC<br>TGTAATCCGACAAGTATCACTGAGGCTGAAATAAGC<br>AAATGGGCATCAGAAAATATTGTTGAATTCTGCGGAT<br>TTAGAAGTGACATTGCTAAGCAGTACTCTAATGCTAA<br>TGTAATATGCTTGCCCTCATATCGAGAAGGGTTACCT<br>AAATGTCTGGTTGAAGCCGCAGCGTGTGGTAGGGCA<br>GTTGTTACAACTGATGTACCAGGTTGCAGGGATGCGA<br>TAGTGGCAAATGTTACTGGGATGTTAGTCGCAGTTCG<br>GGATCCTGTATCGTTAGCAGATGCGATTGAGTTTCTG<br>CTAAAAAATCCAGATGAAAGAATAAAAATGGGGAAG<br>GCGGGGAGATTGTTAGCTGAAAATGAGTACTCAATC<br>GAACATATAGTGAATCAGCACTTATCCATTTACAATG<br>ACTTAATTCACTCCTGA |

EXAMPLE 4

Evaluation of Shiga toxigenic *E. coli* O26:H11

Disclosed oligonucleotides were used to identify Shiga toxigenic *E. coli* O26:H11 in samples of spinach, and ground beef. Results of the each detection is disclosed in FIG. 1.
Spinach Enrichment and DNA Extraction Methods.

In seven enrichment bag, 90 ml of tryptic soy broth was added to 10 grams of spinach. 150 bacterial cells from STEC O26:H11, O45:H2, O103:H2, O111:H8, O121:H19, and O145:NM was added to individual bags, mixed and incubated at 37° C. for 7 hours. No bacteria was added to one bag as a negative control. DNA was extracted using the BAX system lysis buffer (Dupont Qualicon, Wilmington, Del.) as follows. 200 μl of lysis reagent was added to 20 μl of the enriched sample and incubated at 37° C. for 20 minutes. The temperature was increased to 95° C. and incubated for 10 minutes after which the sample was cooled to 4° C. and centrifuged at 20,380×g for 10 minutes. The supernatant was removed and stored at 4° C. 10-fold dilutions of the DNA samples was made and 2 μl used as template for evaluating the serotype specific DNA markers using the Sequenom MassARRAY genotyping system as previously described.
Water Enrichment and DNA Extraction Methods.

In seven enrichment bag, 20 ml of 2× tryptic soy broth was added to 20 ml of water. 150 bacterial cells from STEC O26:H11, O45:H2, O103:H2, O111:H8, O121:H19, and O145:NM was added to individual bags, mixed and incubated at 37° C. for 6 hours. No bacteria was added to one bag as a negative control. DNA was extracted using the BAX system lysis buffer (Dupont Qualicon, Wilmington, Del.) as follows. 200 µl of lysis reagent was added to 20 µl of the enriched sample and incubated at 37° C. for 20 minutes. The temperature was increased to 95° C. and incubated for 10 minutes after which the sample was cooled to 4° C. and centrifuged at 20,380×g for 10 minutes. The supernatant was removed and stored at 4° C. 10-fold dilutions of the DNA samples was made and 2 µl used as template for evaluating the serotype specific DNA markers using the Sequenom MassARRAY genotyping system as previously described.

Ground Beef Enrichment and DNA Extraction Methods.

In seven enrichment bag, 225 ml of tryptic soy broth was added to 25 grams of ground beef. 150 bacterial cells from STEC O26:H11, O45:H2, O103:H2, O111:H8, O121:H19, and O145:NM was added to individual bags, mixed and incubated at 42° C. for 12 hours. No bacteria was added to one bag as a negative control. DNA was extracted by removing 1 ml of the enrichment culture and centrifuging for 5 min at 5,000×g. The supernatant was removed and 200 µl of TE with 50 µg/ml of proteinase K was used to resuspend the pellet. The enriched sample and incubated at 37° C. for 20 minutes followed by 99° C. for 10 minutes after which the sample was cooled to 4° C. and centrifuged at 20,380×g for 10 minutes. The supernatant was removed and stored at 4° C. 10-fold dilutions of the DNA samples was made and 2 µl used as template for evaluating the serotype specific DNA markers using the Sequenom MassARRAY genotyping system as previously described.

EXAMPLE 5

Evaluation of Shiga Toxigenic *E. coli* O45:H2

Disclosed oligonucleotides were used to identify Shiga toxigenic *E. coli* O45:H2 in samples of spinach, and ground beef. Methods for the material preparation is described in Example 4. Results of the each detection is disclosed in FIG. 2.

EXAMPLE 6

Evaluation of Shiga Toxigenic *E. coli* O111:H8

Disclosed oligonucleotides were used to identify Shiga toxigenic *E. coli* O111:H8 in samples of spinach, and ground beef. Methods for the material preparation is described in Example 4. Results of the each detection is disclosed in FIG. 3.

EXAMPLE 7

Evaluation of Shiga Toxigenic *E. coli* O103:H2

Disclosed oligonucleotides were used to identify Shiga toxigenic *E. coli* O103:H2 in samples of spinach, and ground beef. Methods for the material preparation is described in Example 4. Results of the each detection is disclosed in FIG. 4.

EXAMPLE 8

Evaluation of Shiga Toxigenic *E. coli* O121:H19

Disclosed oligonucleotides were used to identify Shiga toxigenic *E. coli* O121:H19 in samples of spinach, and ground beef. Methods for the material preparation is described in Example 4. Results of the each detection is disclosed in FIG. 5.

EXAMPLE 9

Evaluation of Shiga Toxigenic *E. coli* O145:HNM

Disclosed oligonucleotides were used to identify Shiga toxigenic *E. coli* O145:HNM in samples of spinach, and ground beef. Methods for the material preparation is described in Example 4. Results of the each detection is disclosed in FIG. 6.

While the invention has been described with reference to details of the illustrated embodiment, these details are not intended to limit the scope of the invention as defined in the appended claims.

The embodiment of the invention in which exclusive property or privilege is claimed is defined as follows:

1. A method for determining whether a sample contains a Shiga toxin-producing *Escherichia coli* strain by detecting the presence of at least one polymorphism in a O-antigen operon encoding nucleic acid, the method comprising:
   a) providing a nucleic acid sample,
   b) contacting the sample with at least one forward amplification primer and at least one reverse amplification primer,
   c) amplifying a segment of the O-antigen operon encoding nucleic acid of the sample to form an amplified product, wherein the amplified product is hybridized with an oligonucleotide selected from a group consisting of SEQ. ID Nos: 2, 5, and 8 with the oligonucleotide bound by said amplification primers; and
   d) detecting the presence of the amplified product, wherein the presence of the amplified product indicates the presence of a Shiga toxin producing isolate *Escherichia coli* strain.

2. The method of claim 1 wherein the nucleic acid sample is from a meat product.

3. The method of claim 1 wherein the nucleic acid sample is from a vegetable product.

4. The method of claim 1 wherein the Shiga toxin is from *Escherichia coli* strain serotype O26.

5. The method of claim 4 wherein the *Escherichia coli* strain serotype O26 comprises a T at position 30 of SEQ ID NO: 70 (rmla) and a G at position 953 of SEQ ID NO: 71 (wzx).

6. The method of claim 4 wherein the *Escherichia coli* strain serotype O26 comprises a G at position 953 of SEQ ID NO: 71 (wzx) and an A at position 88 of SEQ ID NO: 72 (fnl1).

* * * * *

SEQUENCE LISTING

```
<160> NUMBER OF SEQ ID NOS: 87

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
acgttggatg caggataaag acgagtaccc                                  30

<210> SEQ ID NO 2
<211> LENGTH: 15
<212> TYPE: DNA
<213> ORGANISM: Artificial Sequence
<220> FEATURE:
<223> OTHER INFORMATION: Primer

<400> SEQUENCE: 2
agtacccgaa ccacc                                                  15
```

```
<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
acgttggatg gtgatggtgg agcaagatg                              29

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
acgttggatg taaagggatg aacgcgcttc                             30

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
gagccttata tcccaatata gtaccc                                 26

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
acgttggatg catggttttc attgtcctga g                           31

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
acgttggatg tcatccctgc taaatattcg                             30

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
cctgctaaat attcgtattt cag                                    23

<210> SEQ ID NO 9
<211> LENGTH: 30
<212> TYPE: DNA
<213> ORGANISM: Artificial Sequence
<220> FEATURE:
<223> OTHER INFORMATION: Primer
```

<400> SEQUENCE: 9
acgttggatg tggtggcact ggttcttttg          30

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
acgttggatg cgtatgttac tgatcgtccg          30

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ctcgtccggg ccatgaccgt cg          22

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
acgttggatg tttcaaaggt ctcctgtggc          30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
acgttggatg aaaacaccca gcagacagag          30

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gcagcagaca gagttctgcg a          21

<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
acgttggatg cttttgatcg ctaatgcgat g          31

<210> SEQ ID NO 16
<211> LENGTH: 30

<212> TYPE: DNA
<213> ORGANISM: Artificial Sequence
<220> FEATURE:
<223> OTHER INFORMATION: Primer

<400> SEQUENCE: 16
acgttggatg caacgagttt gtcgctaaag                                              30

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
accaacattg cgggaaa                                                            17

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
acgttggatg ggaatcagat aaattctggc                                              30

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
acgttggatg tcttgttcgt gatggtggag                                              30

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tgatagaacg tctcatcaaa                                                         20

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
acgttggatg cggtattatc ctgacacgag                                              30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
acgttggatg cctggaagct tgtgaaatcg                                30

<210> SEQ ID NO 23
<211> LENGTH: 15
<212> TYPE: DNA
<213> ORGANISM: Artificial Sequence
<220> FEATURE:
<223> OTHER INFORMATION: Primer

<400> SEQUENCE: 23
accggaacta tgtgc                                                15

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
acgttggatg ctatgttacg gcaggccttg                                30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
acgttggatg taccatggag ctagtagacg                                30

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
gcgacaatgt ttgaaaagct aatgcc                                    26

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
acgttggatg aaccacaata agggagcccg                                30

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
acgttggatg ggccgttgtg aagaagagta                                30

<210> SEQ ID NO 29
<211> LENGTH: 23
<212> TYPE: DNA
<213> ORGANISM: Artificial Sequence

```
<220> FEATURE:
<223> OTHER INFORMATION: Primer

<400> SEQUENCE: 29
gaaatgaaag tgttgttttt atg                                              23

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
acgttggatg ggttcgcctt aatccatcag                                       30

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
acgttggatg gcctttcatt ttaccacctc                                       30

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
ttagatatct ttatttaaac aacatctt                                         28

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
acgttggatg caagctcctc atcttcacag                                       30

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
acgttggatg atttaccact ggaacacgcc                                       30

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
gaagttggtc taatcctga                                                   19
```

```
<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
acgttggatg ttctgggtat caccattggg                              30

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
acgttggatg ggaatcagat aaattctggc                              30

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
agaaatatgc acaagtgatt ttt                                     23

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
acgttggatg aaaacgtatc cttcaggctc                              30

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
acgttggatg tagtgcaatc ccaatacgcc                              30

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
catattttgc tttgtgataa ttac                                    24

<210> SEQ ID NO 42
<211> LENGTH: 30
<212> TYPE: DNA
<213> ORGANISM: Artificial Sequence
<220> FEATURE:
<223> OTHER INFORMATION: Primer
```

```
<400> SEQUENCE: 42
acgttggatg tagtgcaatc ccaatacgcc                                    30

<210> SEQ ID NO 43
<211> LENGTH: 30
<212> TYPE: DNA
<213> ORGANISM: Artificial Sequence
<220> FEATURE:
<223> OTHER INFORMATION: Primer

<400> SEQUENCE: 43
acgttggatg aaaaaatcaa taacaataag                                    30

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
tcaataacaa taagaatatt aacctg                                        26

<210> SEQ ID NO 45
<211> LENGTH: 29
<212> TYPE: DNA
<213> ORGANISM: Artificial Sequence
<220> FEATURE:
<223> OTHER INFORMATION: Primer

<400> SEQUENCE: 45
acgttggatg ttcatattta gctaacaag                                     29

<210> SEQ ID NO 46
<211> LENGTH: 31
<212> TYPE: DNA
<213> ORGANISM: Artificial Sequence
<220> FEATURE:
<223> OTHER INFORMATION: Primer

<400> SEQUENCE: 46
acgttggatg gtcaacacca gaaaaaatag c                                  31

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
aacgaagaaa taattaacca aaaaaaaa                                      28

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
acgttggatg aaacgtgaat ataaagaaag                                    30

<210> SEQ ID NO 49
```

```
<211> LENGTH: 30
<212> TYPE: DNA
<213> ORGANISM: Artificial Sequence
<220> FEATURE:
<223> OTHER INFORMATION: Primer

<400> SEQUENCE: 49
acgttggatg ccaaagatgt gagcagttcc                                      30

<210> SEQ ID NO 50
<211> LENGTH: 19
<212> TYPE: DNA
<213> ORGANISM: Artificial Sequence
<220> FEATURE:
<223> OTHER INFORMATION: Primer

<400> SEQUENCE: 50
tagcagttcc gcgagatcc                                                  19

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
acgttggatg ttctggtcgc atttggtaag                                      30

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
acgttggatg taatgtacct gggtgtaggg                                      30

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
tgtagggata taataaatga tggg                                            24

<210> SEQ ID NO 54
<211> LENGTH: 31
<212> TYPE: DNA
<213> ORGANISM: Artificial Sequence
<220> FEATURE:
<223> OTHER INFORMATION: Primer

<400> SEQUENCE: 54
acgttggatg caaatggagg tatcaaaaag c                                    31

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
```

```
acgttggatg gtattgttgt gccttcgagc                                    30
```

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56

```
aaaagagaat atggttacag g                                             21
```

<210> SEQ ID NO 57
<211> LENGTH: 31
<212> TYPE: DNA
<213> ORGANISM: Artificial Sequence
<220> FEATURE:
<223> OTHER INFORMATION: Primer

<400> SEQUENCE: 57

```
acgttggatg cgactcttcg aaaatatcat c                                  31
```

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58

```
acgttggatg aaaggccata atgagctgcg                                    30
```

<210> SEQ ID NO 59
<211> LENGTH: 19
<212> TYPE: DNA
<213> ORGANISM: Artificial Sequence
<220> FEATURE:
<223> OTHER INFORMATION: Primer

<400> SEQUENCE: 59

```
ttaacgttga agcagcaag                                                19
```

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60

```
acgttggatg ggtaaatcta agcttgttgc                                    30
```

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61

```
acgttggatg ctccttggtc ttaaatgggc                                    30
```

<210> SEQ ID NO 62
<211> LENGTH: 21
<212> TYPE: DNA

```
<213> ORGANISM: Artificial Sequence
<220> FEATURE:
<223> OTHER INFORMATION: Primer

<400> SEQUENCE: 62
cctgtttttg tcgatattga t                                             21

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
acgttggatg gcctcttcaa ttcttctcgg                                    30

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64
acgttggatg aatgggtatc agcagagtgg                                    30

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
gcagagtgga actaattttg                                               20

<210> SEQ ID NO 66
<211> LENGTH: 30
<212> TYPE: DNA
<213> ORGANISM: Artificial Sequence
<220> FEATURE:
<223> OTHER INFORMATION: Primer

<400> SEQUENCE: 66
acgttggatg tttcaaaggt ctcctgtggc                                    30

<210> SEQ ID NO 67
<211> LENGTH: 30
<212> TYPE: DNA
<213> ORGANISM: Artificial Sequence
<220> FEATURE:
<223> OTHER INFORMATION: Primer

<400> SEQUENCE: 67
acgttggatg agtagcctgg aggccattac                                    30

<210> SEQ ID NO 68
<211> LENGTH: 17
<212> TYPE: DNA
<213> ORGANISM: Artificial Sequence
<220> FEATURE:
<223> OTHER INFORMATION: Primer

<400> SEQUENCE: 68
gaggccatta ctacagt                                                  17
```

```
<210> SEQ ID NO 69
<211> LENGTH: 30
<212> TYPE: DNA
<213> ORGANISM: Artificial Sequence
<220> FEATURE:
<223> OTHER INFORMATION: Primer

<400> SEQUENCE: 69
acgttggatg gagctgtttt taccgacaga                                        30

<210> SEQ ID NO 70
<211> LENGTH: 879
<212> TYPE: DNA
<213> ORGANISM: Artificial Sequence
<220> FEATURE:
<223> OTHER INFORMATION: Primer

<400> SEQUENCE: 70
atgaaaacgc gtaaaggtat tattttagct ggtggttcgg gtactcgtct ttatcctgta       60
actatggctg tcagtaaaca gttgttaccg atttatgata aaccgatgat ctattacccg      120
ttgtctacac tgatgttagc gggtcttcgc gatattctga ttattagtac gccacaggat      180
actcctcgtt ttcaacaact gctgggtgac gggagccagt gggggctaaa tcttcagtac      240
aaagtgcaac cgagtccaga tggtcttgcg caggcattta tcatcggtga agagtttatc      300
ggtggtgatg attgtgcttt ggttctaggt gataatatct tttacggtca cgatctgccg      360
aagttaatgg atgtcgctgt taacaaagaa agtggtgcaa cggtatttgc ctatcacgtt      420
aatgatcctg aacgctacgg tgtcgttgag tttgataaaa acggtacggc gatcagcctg      480
gaagaaaaac cgctacaacc aaaaagtaat tatgcggtaa ccgggcttta tttttatgat      540
aactacgttg tcgaaatggc gaaaaatctt aagccttctg cccgcggtga actggaaatt      600
accgatatta accgtattta tatggaacag gggcgtttat ccgttgccat gatgggacgt      660
ggttatgcat ggctggacac ggggacacat caaagtctta ttgaggcaag caattttatc      720
gcaacaatag aagaacgtca ggggctgaaa gtttcctgcc cggaagaaat tgcttaccgt      780
aaagggttta tcgatgctga gcaggtgaaa gtattagctg aaccgttgaa gaaaaatgct      840
tatggtcagt atctgctgaa aatgattaaa ggttattaa                             879

<210> SEQ ID NO 71
<211> LENGTH: 1263
<212> TYPE: DNA
<213> ORGANISM: Artificial Sequence
<220> FEATURE:
<223> OTHER INFORMATION: Primer

<400> SEQUENCE: 71
atgttgaaaa aaaacttca aaaaataaag gaatatcatt cagtattgga gttggcaata       60
attcagggtg cgaatgccat atttcctgtg ttggtattcc catttttct tattaccttta     120 ggggaaaaca tcttttcaag tattgctgtt ggtgaagtac tagcactata tgtgcttata      180
ttttcgctat acagttttga tattataagt gtgcagaagg taatttcaag tgtgacaaaa      240
gatgaaatat ttaaagttta cattctgaca ctaatctgta ggttgtgttt atttgttatt      300
tcaggaatat gtcttttatt tataacgtat ttaattaata aaacattaag tgtatacttg      360
ggattgtttt tattgtaccc agtagggatg atattgcaat ctaattattt ttttcaggct      420
acgaataaca ataggccatt ggctgttttt gtactaattg ctcgtggtat gtcattatgt      480
```

-continued

| | |
|---|---|
| cttatttatt tttataatgg accagcaggc tatttaacaa gttattatta tgtcatttgt | 540 |
| gtgtctggtt cgtattttt atctggcgtg ctatcgctta tatatatata ttatcaaaat | 600 |
| aagactaata aagctaaaat tcaatgggcg gaaattttag aatatatatg cacaggttat | 660 |
| catctgttta ttgctaatat atttgttatt ctatacagaa atagtaatat tattattctt | 720 |
| ggcactcttg cttcgcctgt tgcaacgtct ctgtacgcga cggcagagaa aattattaaa | 780 |
| tgtattcagt ctatagcaac cccgttaaat caatactatt tcacgaggtt gataaagcaa | 840 |
| catgaattga aattagaacc atacaaagtt ggagaatata aaagcctgct atatgcaagc | 900 |
| acaaatattc agctaaagtt catggttttc attgtcctga gtttaggggg ggtgggtact | 960 |
| atattgggat ataaggttca aagtatcgct gaaattagaa gcgcgttcat ccctttatca | 1020 |
| ataatgtctt ttgcaatatt tatggggata tacaatttta tgtttggttc ggttggattg | 1080 |
| tccataagag ggtataaaaa agaattttct tatatagtgg ccattacggg tgtttcaact | 1140 |
| attattttat cattatgcct gagttatttc tttgctgaaa taggcgctgc aattgcttat | 1200 |
| gtatttgctg agtttatctt acttattctc atacttagaa tttataaagt gaaacgatta | 1260 |
| taa | 1263 |

<210> SEQ ID NO 72
<211> LENGTH: 1035
<212> TYPE: DNA
<213> ORGANISM: Artificial Sequence
<220> FEATURE:
<223> OTHER INFORMATION: Primer

<400> SEQUENCE: 72

| | |
|---|---|
| atgtttaaga ataaaacact cgttatcact ggtggcactg gttcttttgg taatgccgta | 60 |
| cttaagcgtt ttctagatac agatattact gaaatacgaa tatttagcag ggatgaaaaa | 120 |
| aaacaagatg atatgcggaa aaaatataat aactcaaaat taaaatttta tataggtgat | 180 |
| gtgcgagact ataattccgt tctaaatgca acgcgtggtg ccgattttct gtatcatgca | 240 |
| gcagccctta acaagttcc ttcatgtgaa tttcacccta tggaggcggt taagacaaat | 300 |
| gttctgggta cggaaaatgt tctggaggct gctattgcga atgggattaa acgcgtggtg | 360 |
| tgcttgagta ccgataaagc cgtttatcct atcaatgcaa tgggcatatc taaggcaatg | 420 |
| atggaaaaag ttattgttgc aaaatcacgt aatcttgaca gttcaaaaac agttatctgt | 480 |
| ggaactcgtt atggaaatgt aatggcttca cgtggatcgg tcatcccatt atttgttgat | 540 |
| ctaatcaaag ctggtaaacc attgaccata accgatccca atatgactcg tttcatgatg | 600 |
| acgcttgagg atgctgtcga tctggtcctt tatgctttcg aacatggaaa taatggtgac | 660 |
| atttcgttc agaaagcacc tgcggcaaca attcaaacat tagccattgc acttaaggaa | 720 |
| ttgctaaatg cccatgagca tccaatcaat attattggaa ctcgacacgg ggaaaaactt | 780 |
| tacgaagcgt tattgagccg agaggaaatg attgcagcgg aagatatggg tgattattat | 840 |
| cgtgttccac cagatctccg cgatttgaac tatgaaaaat atgtggaaca tggtgaccgt | 900 |
| cgtatctcgg aagtggaaga ttataattct cataatactg agagattaga tgttgaggga | 960 |
| atgaaagaat tactgctaaa acttcctttt atccgggcac ttcgttctgg tgaagattat | 1020 |
| gagttggatt cataa | 1035 |

<210> SEQ ID NO 73
<211> LENGTH: 1140
<212> TYPE: DNA
<213> ORGANISM: Artificial Sequence
<220> FEATURE:
<223> OTHER INFORMATION: Primer

<400> SEQUENCE: 73

```
atgctcaggt tcagaacgc cagtatccag acaaatacac tagacggaac agataacgtg      60
aaaattcttg tgacgggggg ggccggcttt atcggctcag cggttgtacg acatattatt    120
aaaaatacccc aggacgacgt cgtcaatgta gataagctga cctatgccgg caaccttgag   180
tcgctgagtg aagtcagcga cagcgatcga tatgcttttg agcatgcgga tatttgcgat   240
aaagatgcta tggatcgcat tttagcaaag cataagcctg atgcggtgat gcatttggcg   300
gctgaaagtc atgtcgatcg ttctattacc ggcccggcgg cttttatcga accaatatc    360
gttggcactt atgtgcttct ggaagccgcc cgggcttact ggtcaacgtt ggatgagcaa   420
gcgaagaaag cgttccgttt tcatcacatt tctaccgacg aagtgtatgg tgatttgccg   480
catcctgatg aacatcccgc atcaactgag ctgtcactct tcactgaaac caccgcatat   540
gcacctagca gcccatattc agcgtcgaaa gcctcgagcg accatctcgt tcgtgcctgg   600
ttgcgcacct atggtttccc gaccattgtc accaactgtt caaataacta tggcccgtat   660
catttccctg aaaaactgat ccctctggtt attctgaatg cgctggacgg taaagttttg   720
cctatttacg gcaaggggga ccagattcgt gactggctgt acgttgaaga ccacgcccgc   780
gcactctaca ccgttgtcac tcaggggaaa ccgggtgaaa cgtacaatat tggcggtcat   840
aacgaaaagc agaacttgga tgtggtccat acgatttgcg atctgcttga tgagattgtg   900
ccaaaagagg gatcttatcg cgatcagata acgtatgtta ctgatcgtcc gggccatgac   960
cgtcgctacg ccattgatgc aaataaaatt agtgctgagt tgggatggac gccacaggag  1020
acctttgaaa gtggtattcg taaaaccgtt gaatggtatt tgacaaatac agaatgggtg  1080
gaaaacgtta aagcggtaa ttataaatcc tggattgcgc aaaattatca aaatcgttaa  1140
```

<210> SEQ ID NO 74
<211> LENGTH: 1035
<212> TYPE: DNA
<213> ORGANISM: Artificial Sequence
<220> FEATURE:
<223> OTHER INFORMATION: Primer

<400> SEQUENCE: 74

```
atgttatatc tgggcattgt cgttttttgca ttctttatat catgcgcgtt gacttggggt      60
ttaaggttat atgccatcaa gaataatgta attgatcaac caaaccaaag aagttctcac    120
agtgttccta cgcctcgtgg gggagggggtg gctattgtat taacattgtt ggcttcatta   180
atatggctgg tccttacaaa tcatataact caggcaacat ttttaggttt cttcgtgact   240
ggcttattga ttgcggttat tggtttcctc gacgatcatg gccatatcgc tgcacgctgg   300
cgcttgttaa tgcatttcat cgctgcagct atagggcttt tttatctagg atctttccca   360
agcattaata tgtttggcta cgatgtttct ttgtcatggt ttggaatgat cctcggtagt   420
atctatcttg tatggatgtt gaatttatat aactttatgg atggtattaa tggtcttgca   480
agtgcgcaag ctattacctt ttcgctttgt agtatcttga taataactat caataactac   540
tctgattcat ctgatgcaat gactatgctt gcattagcac tcgctggatc ggtcgcggga   600
ttcatcgtgt ggaacttccc tgtggcaagg atcttcatgg gcgatgctgg aagcggtttt   660
ctgggtatca ccattgggct gatgatcctt tattttgcaa agctagactc acgtgttctg   720
atcgcagaac tctgtctgct gggtgttttc attgttgatg caactactac cttactgaga   780
```

| | |
|---|---|
| agattactgg cgggtaagaa agtctatgaa gcacatgcaa gtcattgtta ccaaattctt | 840 |
| gcccgtaaat ataagagcca tgttcctgtt actatggcgg ctatagctat taacttcatg | 900 |
| tggctgctcc ctattgctta cttaatcatc tctgcaaaaa ttgatggaat tgtaggcatt | 960 |
| accatcgctt ggttaccatt gatgattctt gcattcagat gtggtgctgg agttaaagat | 1020 |
| aaagagaggg cataa | 1035 |

<210> SEQ ID NO 75
<211> LENGTH: 966
<212> TYPE: DNA
<213> ORGANISM: Artificial Sequence
<220> FEATURE:
<223> OTHER INFORMATION: Primer

<400> SEQUENCE: 75

| | |
|---|---|
| ttggtgcagt acaatgataa gatttcaata gtggtccctg cctattgtga accatcgaaa | 60 |
| gttaagcgtt tcatggatgc catactgaat attgattatc cagataacct tattgaatta | 120 |
| attcttattg acgattgtag tccggtttca ctggaagaaa tcgcagcctc ttatggagaa | 180 |
| gtctttaaag ataaaataaa ttttttattc cacaggaatc agataaattc tggcagggct | 240 |
| atttcccgca atgttggtat ttcttttagcg acaaactcgt tgataatgtt tattgatatc | 300 |
| gataacctgc ttgaacctta tgcaataaaa aaaattgttt cttttttcca tggtaagcac | 360 |
| ttcactgcag ccagaattaa tatacgaatc gaccctgcca gactttccac tagcaattat | 420 |
| ctccgttatt tgatagccg ttatctcgga gcgcgtaata tccctgaagg gatcataagt | 480 |
| actcgtttct tgcaagtgca cggtattatc ctgacacgag acatcattaa tacaatcggt | 540 |
| ggttttgatg agacgttcta tcattacggc tgtgaagatg aggagcttgg aatccgagtt | 600 |
| tcaaaagcga aatatgactt ttatttttta cccaatgcaa aggcagaaga cagtgataca | 660 |
| ccaacattgc gccgagcatc agaaagaatg gttgtgtatg catcaaaatc tttccctgta | 720 |
| ttgaaagaaa aacacccgga gtgcgtgaag atagtctct tttcatccta cgaggtaatg | 780 |
| ttagatgata cgagactccg cagtaaatta ctcataaatg ttattcatct tcttcctctt | 840 |
| acaacaaccc gcaaaagcct tctttggttg tgtgataaat tagatgcaaa agcgattaaa | 900 |
| gttcctgact tcatatataa gttcgtattg gcactttcat atattgaagg tggaaaactt | 960 |
| cggtag | 966 |

<210> SEQ ID NO 76
<211> LENGTH: 1149
<212> TYPE: DNA
<213> ORGANISM: Artificial Sequence
<220> FEATURE:
<223> OTHER INFORMATION: Primer

<400> SEQUENCE: 76

| | |
|---|---|
| atgagtattt ttttaatgtc cccagggttt gtgtatgctt caatttggct gttcacaatt | 60 |
| atattatatt cgcttggagt gactactaat attagcccgc tctcaaatga gatggtggtg | 120 |
| tttttatcaa ttaatgttac tctgggtttg atttttttcac ttccatttat tactcctggc | 180 |
| agtattaatc gcgttcgtct ggatgaaatt atgccatctt ggcgagcgac taaaatatgg | 240 |
| ctcatcattt ggtgctttgt gataattcct gatgtggttg ctgctggcgg gataccaatg | 300 |
| attatgcaat ttaggggcgg ctataattat accgagttcg gtataccgac atatcatggg | 360 |
| atagttaata tgctattcct ttttgttttt ccgtcactgt attatcattt tcttttatca | 420 |
| aaaagaaaaa ttattctgct gattatacta ttgatgagta tatgggaaat gctggtcttc | 480 |

-continued

```
agacgaggta tactgatgtc aggcctcgtg gaaatattct tttattttt tatctataaa      540 aaattcacta aaaagatgtt tatttataca gtattttctg taatcacaat agttctactt      600
tttggagctg taggagatat caggggcgct gaaaatcctt atcaatattt gttgtcacca      660
gaaggacaat ttctgtcgag tttgccttca ggcttcacat ggttttatgt ctatgttacg      720
gcaggccttg caaaccttgc ataaactttt gcgcacatag ttccggtata cgatttcaca      780
agcttccagg acctattccc cagtgttatc agaaatctca tttacagtga tttaggattc      840
catgatacca tggagctagt agacgataat gccaacgttt cgacaatgtt tgaaaagcta      900
atgcccgatc ttgggatcgc gggctccctt attgtggtta catgtttact tctgcttttt      960
agtattgctt acaagaattt gcttaaatcg tatcattata gtttatttcc ttatgcgatt     1020
gcaatgcaat gtgcaatatt cagtggcttt tataatttat tctttattca aacatatttt     1080
ttacttttca ttgttactct tgttttgtg agaattaaaa tatttacagg gagccattct      1140
catgtttga                                                             1149
```

<210> SEQ ID NO 77
<211> LENGTH: 1011
<212> TYPE: DNA
<213> ORGANISM: Artificial Sequence
<220> FEATURE:
<223> OTHER INFORMATION: Primer

<400> SEQUENCE: 77

```
atgaaagtgt tgtttttatg tcctcgtttt tttaactatg aaaatgaaat atctgatgga       60
ttaaggcgaa ccggtgccac cgttgattat ttcgatgaga aaccatttaa taacgtattt      120
tttaaaatat tactcagact ttggaaaggt aataatttta ttaaacgtat ttcagacgcg      180
tattttgaga agattttgct tcaaacaaat gatgactatg attacgtcat agtactcaaa      240
ggtgaatctc ttgatagaaa aaatttattg aaattcaaaa ataaatataa gaacgctaaa      300
ttcatttatt acgcatggga ttctattaaa aactaccctc atattcaaga gtgcctgaat      360
ttatttgacc gcgtatttac ctttgatgat aacgatgcgc gagaatatga ttttatgact      420
catttgccat tgttttattc cccggatttt gtaagcacac cgaaaaaaga agcttcaaag      480 aatttttaagc catctattgc atttctcggt accgtacata gtgacagata cagagtattg      540
ggagaggttt atgagaaata taaaatgaa tatgatttga ggtttgttct ttatttccct      600
tcaattgttg tcttggtagg ttttcttctt actaattta agtcaatcat taggttcaaa      660 cttttagtt ttaccttcg ctctagaagt aaaaagcaga tagcatcatt cttctctagt      720
gctgatgcgg tccttgatat ccagcatccc cgtcagacag gtttgacgat gaggacaata      780
gaatgcttgc ctctcaagag gaaatttata actaccaatt cacgagttaa aaattacgat      840
ttttattccg ctgaaaattt ttactttatc gatcgagata atatccttat cgactctgat      900
tttttcgaaa tccatataaa cgatgcgcac ctagatgcaa tttcgcgtta tagtatagac      960
tcgtgggtaa aacattatg ttcgactcat atcagagaag atgttgttta a              1011
```

<210> SEQ ID NO 78
<211> LENGTH: 1509
<212> TYPE: DNA
<213> ORGANISM: Artificial Sequence
<220> FEATURE:
<223> OTHER INFORMATION: Primer

<400> SEQUENCE: 78

-continued

```
tagttattgt tatctaacaa tatcatatct ttcatgggga tctagtaata attctaaaat      60
gaaagcaaaa tattttttct ttacctctgt acttctgtta ccttctgcgt tctccgcgaa     120
aaacagcaat gcaattttct cttaggcacg gtatcatcat cctactaagt tgaaggtggt     180
tggaataaaa atggaaaggg gccttcagat tgggattatt ttacccataa tgaggtcaca     240
aaatatacca ttggcactgt tggaaattta ccactggaac acgccattag cactttataa     300
aaaaggaagt tggtctaatc ctgaatcacc agtttggttt gagaaatatg cacaagtgat     360
ttttgaaaat tttggtagca gaagttatta ttttctaact tttaatgagc ctgaaggata     420
cgttttact caggaacctc ttgcagcaaa ccttattgat aaaaagctag acggatatcg     480
tgatgtttta tccgttgttt ctcgtggaaa ataagcgata gcatttcaca atcttttgat     540
cgctaatgcg atggttgtac gtaattatca caaagcaaaa tatgatggac gtattggcgt     600
attgggattg cactaaactt atcgccaagc attgataatg accaaccaaa tagtgctact     660
gagaagttat gaaacgatat tcataacaac tagattctgg atgttattta taagagggaa     720
taccctcatt cagtattgaa aatgtattag tctacatatc ctaaattcaa gcctacattt     780
caagatatgc aattcattac ctagggaaaa cctgatttta tcggcgtaaa ttgttatggt     840
ccaacattgg ttaagtatga taaatctgaa ccgtttgaaa tatgtaacgt tcaaatcca      900
gataaagggc cttctgtcaa cggtccattc tctccagagg cgctggtaat gatgatgaaa     960
aagtttgata tacaatattc gcatcctacc ttcattatta ctgagtatgg tgcaggtttt    1020
ggtttagccg ataaaaaatt taatgatggc attatttctg ataagttgcg agtagactat    1080
ctcaagagat atgtatctgc agttattgaa gcaaaaaaga aggtttagat atccatggct    1140
atctattttg gagcttgctt gataatttcg aatagttata gggttacaaa ataggtttg     1200
gcataattgg tgttgatttt aatgataagg ctttgaagcg aacaccggag ttaagctatt    1260
atagctacca gaaaattatt aaagaaaata aaatcaatg tgttttattg atgagaaaat     1320
aatccacaat aaaccatgtc ttttgttaag gcttaagtgt gtcaatgacc ataattacct    1380
acctctgctc tcgatttctg agttaagata attcgataat atatccaccg ggaagtaccc    1440
cggtgggagc acacctgaca ggagtatgta atgtcaaagc aacagatcgg cgtcgtcggt    1500
atggcagtg                                                            1509
```

<210> SEQ ID NO 79
<211> LENGTH: 987
<212> TYPE: DNA
<213> ORGANISM: Artificial Sequence
<220> FEATURE:
<223> OTHER INFORMATION: Primer

<400> SEQUENCE: 79

```
atgataatat cttcagataa cctaagtgtt attatcccag tttataatga agagaagaat      60
gttattaata ttcttcaatc tcttgaatgc cagtctttaa cgggatttaa tgttattgtc     120
attgatgatg gttcaaaaga tatgactgct tctcttgtaa agaatataaa accatcatca     180
tatagtttaa gcttaataca acaaagtaat atggggggctg ctcgggcaag ggagaatgcc    240
atcaatttta ctcatagtga gtatattgca tttatagata gtgatgactc tttaagttca    300
gatgctcttg aaaaagcatt agctccgatg ctggataata agatatcga catctcacta    360
tttgaactgg tacatattaa aaacttaaat catgatacta ataacatatt tgtaccttat    420
tctacaacca aattaatatg tggagaagag gcttttgcta attgtatttc atattgggga   480
ttgcatgggt ttggtatcta caaagaaaa ttgattcaaa aatcctatgg tatttattat    540
```

| | |
|---|---|
| aaatataata aaaacaaaga aaattatata aataatgatg aggttatttc aagaatcagt | 600 |
| tttggattat ctaaaaatat ctatttatca tctggaagat atttctttgt acagaacatg | 660 |
| gattcaacaa caagaagaat aaatgaaagt tattataaag ttataaataa tgctgtttat | 720 |
| ttaagagagt atatagatga agaaataaaa tataatgatt ttgattgtct aggtgaagct | 780 |
| aataaactcc ttgtaagtac tatatgggga gtgtttgttc gttatcaaaa atggaagaaa | 840 |
| aaattcagtg atgaaacaaa cggtaaatgg cgcgaagcaa taaaaaaagg aatgcaaatg | 900 |
| ataaaaaaaa tcaataacaa taagaatatt aacctgcata ttaaatctaa aatgcaatta | 960 |
| tatataatat ctaaacttgt tagctaa | 987 |

<210> SEQ ID NO 80
<211> LENGTH: 1188
<212> TYPE: DNA
<213> ORGANISM: Artificial Sequence
<220> FEATURE:
<223> OTHER INFORMATION: Primer

<400> SEQUENCE: 80

| | |
|---|---|
| gtgaatataa agaaagataa gtttataaat ggagtgcttt ttttttggtt aattatttct | 60 |
| tcgttatatt acttaaatgc tatttttttct ggtgttgaca cattaaaata taatgaagat | 120 |
| ttaacgcaaa aaattataaa atatatagtt tgcttagtta taagtctaag tatcttattt | 180 |
| atttacaaga aatttaatta ttttttttgta ttgttttttt tcttgttcct gtctgttgct | 240 |
| tcagcccttt tcagtggtgc ggtaacaatt tacgcaacaa caatgttgat tattgcaact | 300 |
| atgatcagct tttgcctgat tattcctcta tttttcttata atatggtgaa agttaataga | 360 |
| gttcttttat ggacaggagt tattgtaggc acgatttctg tattagaatt aacggtattt | 420 |
| tataattata tggtttcata ttgggctgcc actgatggga ttaggtcaat atcttctctt | 480 |
| ctgaatccta cgaatagtgg tgcttattca gcgattatta ttttaatcgc cttggtgaca | 540 |
| aatataaaaa gtcttttttaa aagagcttta tttcttataa tgccgatgat aacgttaatt | 600 |
| agcagtggtt cgcgcacagc atggttatca cttggtatga cactttttatt aacagtagta | 660 |
| ttgagagaca gtgccagcat tcgcttgcga aaaaaaatat ttactcttgc aagcattggc | 720 |
| actgtttgcg gtgcattgta cgccatattt tatatgggca gtatctctgg tattgaatca | 780 |
| caatatcgag gtcttaatac gtatactgca tcaattcgag ttgaaaactt tctgacatat | 840 |
| ttaaatttag ttgatctgaa tatgttgcta cctgattttt tagataaaaa tataaatctc | 900 |
| atttcagata actttttatct cgtaatgttt aattatgccg gtctaatcgg cttttttatt | 960 |
| gtttttattaa ttttattgct gcttatcttc tggaacatac aatttaaaat atttaatgag | 1020 |
| ttaatggctg aagatatagc catttggaga gttgttttta tttatttcct aatatccggg | 1080 |
| ctttcaaatt catttataaa ttcttttcct gtaaatcaat tgttctttat ctcatgcgga | 1140 |
| tattatatat ataaatataa attagttaaa agctctatag gaagataa | 1188 |

<210> SEQ ID NO 81
<211> LENGTH: 465
<212> TYPE: DNA
<213> ORGANISM: Artificial Sequence
<220> FEATURE:
<223> OTHER INFORMATION: Primer

<400> SEQUENCE: 81

| | |
|---|---|
| agatttacac gtctttgtga cgataagcca gaaaaaatag cggcagttaa catccaggct | 60 |

| | |
|---|---|
| tctatgcttt aagcaatgga atgttactgc cgttttttat gaaaaatgac caataataac | 120 |
| aagttaacct accaagttta atctgctttt tgttggattt tttcttgttt ctggtcgcat | 180 |
| ttggtaagac aattagcgtg agttttagag agttttgcgg gatctcgcgg aactgctcac | 240 |
| atctttggca tttagttagt gcactggtag ctgttaagcc aggggcggta gcttgcctaa | 300 |
| ttaattttta acgtatacat ttattcttgc cgcttatagc aaataaagtc aatcggatta | 360 |
| aacttctttt ccattaggta aaagagtgtt tgtagtcgct cagggaaatt ggttttggta | 420 |
| gtagtacttt tcaaattatc catttttccga tttagatggc agttg | 465 |

<210> SEQ ID NO 82
<211> LENGTH: 1194
<212> TYPE: DNA
<213> ORGANISM: Artificial Sequence
<220> FEATURE:
<223> OTHER INFORMATION: Primer

<400> SEQUENCE: 82

| | |
|---|---|
| atgttactat gctgcataca tatcaatgta tattatttac ttttagaatg tgatatgaaa | 60 |
| aaaatagtga tcataggcaa tgtagcgtca atgatgttaa ggttcaggaa agaattaatc | 120 |
| atgaatttag tgaggcaagg tgataatgta tattgtctag caaatgattt ttccactgaa | 180 |
| gatcttaaag tactttcgtc atggggcgtt aaggggggtta aattctctct taactcaaag | 240 |
| ggtattaatc cttttaagga tataattgct gtttatgaac taaaaaaaat tcttaaggat | 300 |
| atttccccag atattgtatt ttcatatttt gtaaagccag taatatttgg aactattgct | 360 |
| tcaaagttgt caaagtgcc aaggattgtt ggaatgattg aaggtctagg taatgccttc | 420 |
| acttattata agggaaagca gaccacaaaa actaaaatga taaagtggat acaaattctt | 480 |
| ttatataagt tagcattacc gatgcttgat gatttgattc tattaaatca tgatgataaa | 540 |
| aaagatttaa tcgatcagta taatattaaa gctaaggtaa cagtgttagg tgggattgga | 600 |
| ttggatctta atgagttttc atataaagag ccaccgaaag agaaaattac ctttattttt | 660 |
| atagcaaggt tattaagaga gaagggata tttgagttta ttgaagccgc aaagttcgtt | 720 |
| aagacaactt atccaagttc tgaatttgta attttaggag ttttgagag taataatcct | 780 |
| ttctcattac aaaaaaatga aattgaatcg ctaagaaaag aacatgatct tatttatcct | 840 |
| ggtcatgtgg aaaatgttca agattggtta gagaaaagtt ctgttttttgt tttacctaca | 900 |
| tcatatcgag aaggcgtacc aagggtgatc caagaagcta tggctattgg tagacctgta | 960 |
| ataacaacta atgtacctgg tgtagggat ataaaaatg atggggtcaa tggcttttg | 1020 |
| atacctccat ttgaaattaa tttactggca gaaaaaatga atattttat tgagaataaa | 1080 |
| gataaagtac tcgaaatggg gcttgctgga aggaagtttg cagaaaaaaa ctttgatgct | 1140 |
| tttgaaaaaa ataatagact agcatcaata ataaaatcaa ataatgattt ttga | 1194 |

<210> SEQ ID NO 83
<211> LENGTH: 1167
<212> TYPE: DNA
<213> ORGANISM: Artificial Sequence
<220> FEATURE:
<223> OTHER INFORMATION: Primer

<400> SEQUENCE: 83

| | |
|---|---|
| atgattacat acccacttgc tagtaatact tgggatgaat atgagtatgc agcaatacag | 60 |
| tcagtaattg actcaaaaat gtttaccatg ggtaaaaagg ttgagttata tgagaaaaat | 120 |
| tttgctgatt tgtttggtag caaatatgcc gtaatggtta gctctggttc tacagctaat | 180 |

```
ctgttaatga ttgctgccct tttcttcact aataaaccaa aacttaaaag aggtgatgaa    240
ataatagtac ctgcagtgtc atggtctacg acatattacc ctctgcaaca gtatggctta    300
aaggtgaagt tgtcgatat caataaagaa actttaaata ttgatatcga tagtttgaaa    360
aatgctattt cagataaaac aaaagcaata ttgacagtaa attattagg taatcctaat     420 gattttgcaa aaataaatga gataataaat aatagggata ttatcttact agaagataac    480
tgtgagtcga tgggcgcggt ctttcaaaat aagcaggcag gcacattcgg agttatgggt    540
acctttagtt cttttactc tcatcatata gctacaatgg aagggggctg cgtagttact     600
gatgatgaag agctgtatca tgtattgttg tgccttcgag ctcatggttg acaagaaat    660 ttaccaaaag agaatatggt tacaggcact aagagtgatg atattttcga agagtcgttt    720
aagtttgttt taccaggata caatgttcgc ccacttgaaa tgagtggtgc tattgggata    780
gagcaactta aaaagttacc aggttttata tccaccagac gttccaatgc acaatatttt    840
gtagataaat ttaagatca tccattcctt gatatacaaa aagaagttgg tgaaagtagc    900
tggtttggtt tttccttcgt tataaaggag ggagctgcta ttgagaggaa gagtttagta    960
aataatctga tctcagcagg cattgaatgc cgaccaattg ttactgggaa ttttctcaaa    1020
aatgaacgtg ttttgagtta ttttgattac tctgtacatg atacggtagc aaatgccgaa    1080
tatatagata agaatggttt ttttgtcgga aaccaccaga taccttttgtt taatgaaata    1140 gattatctac gaaaagtatt aaaataa                                        1167

<210> SEQ ID NO 84
<211> LENGTH: 1266
<212> TYPE: DNA
<213> ORGANISM: Artificial Sequence
<220> FEATURE:
<223> OTHER INFORMATION: Primer

<400> SEQUENCE: 84
atggtattaa cagtgaaaaa aattttagcg tttggctatt ctaaagtact accaccggtt     60
attgaacagt ttgtcaatcc aatttgcatc ttcattatca caccactaat actcaaccac    120
ctgggtaagc aaagctatgg taattggatt ttattaatta ctattgtatc tttttctcag    180
ttaatatgtg gaggatgttc cgcatggatt gcaaaaatca ttgcagaaca gagaattctt    240
agtgatttat caaaaaaaaa tgctttacgt caaatttcct ataattttc aattgttatt    300 atcgcatttg cggtattgat ttctttttctt atattaagta tttgtttctt cgatgttgcg    360 aggataatt cttcattctt attcgcgatt attatttgtg gttttttca ggaagttgat     420 aatttattta gtggtgcgct aaaaggtttt gaaaaattta atgtatcatg ttttttttgaa    480 gtaattacaa gagtgctctg ggcttctata gtaatatatg gcatttacgg aaatgcactc    540
ttatatttta catgtttagc ctttaccatt aaaggtatgc taaaatatat tcttgtatgt    600
ctgaatatta ccggttgttt catcaatcct aattttaata gagttgggat tgttaatttg    660
ttaaatgagt caaaatggat gtttcttcaa ttaactggtg gcgtctcact agtttgttt    720 gataggctcg taataccatt gattttatct gtcagtaaac tggcttctta tgtcccttgc    780
cttcaactag ctcaattgat gttcactctt tctgcgtctg caaatcaaat attactacca    840
atgtttgcta gaatgaaagc atctaacaca tttccctcta attgttttttt taaaattctg    900 cttgtatcac taatttctgt tttgccttgt cttgcgttat tctttttttgg tcgtgatata    960 ttatcaatat ggataaaccc tacatttgca actgaaaatt ataaattaat gcaaatttta    1020
```

| | |
|---|---|
| gctataagtt acattttatt gtcaatgatg acatcttttc atttcttgtt attaggaatt | 1080 |
| ggtaaatcta agcttgttgc aaatttaaat ctggttgcag ggctcgcact tgctgcttca | 1140 |
| acgttaatcg cagctcatta tggcctttat gcaatatcta tggtaaaaat aatatatccg | 1200 |
| gcttttcaat tttattacct ttatgtagct tttgtctatt ttaatagagc gaaaaatgtc | 1260 |
| tattga | 1266 |

<210> SEQ ID NO 85
<211> LENGTH: 1104
<212> TYPE: DNA
<213> ORGANISM: Artificial Sequence
<220> FEATURE:
<223> OTHER INFORMATION: Primer

<400> SEQUENCE: 85

| | |
|---|---|
| atggaaaagc aatctttgt aacgcaacct aatttaccac cgctagagga gtttatacca | 60 |
| tatctggaaa tcatttggca gaataagcaa tttacaaata atggtccaat gcatcaaaaa | 120 |
| ttagaaaaaa aattatgcga gtttcttggt gttgaataca ttagtctatt taataatggg | 180 |
| actattgcgc ttataaccgc agtacaggct ttgggtgtta aggcgaagt aattaccaca | 240 |
| ccatattcct ttgtagcaac tgcacactcc ttggtcttaa atgggcttaa acctgttttt | 300 |
| gtcgatattg attccaaaac cttaaatatc gatccgagaa gaattgaaga ggcgattacc | 360 |
| cctgaaacgc aggcaataat gccggtgcac tgctatggga atccttgcga tacacaagct | 420 |
| attgctgata ttgcgcaaaa atataattta aaggtcattt atgatgctgc gcatgccttt | 480 |
| ggcgttgaag atgatgatgg aagtgttctt cgccatggag atctaagtgt cttaagtttc | 540 |
| catgcaacta agtgttcag cacttttgaa ggcggagcta ttgtgtgtaa tagtaaagaa | 600 |
| atgaaagaaa aaattgatag actaaaaaac tttggttata tcgatgaaac taacatcaat | 660 |
| atcattggct ctaatggaaa aatgagcgaa gttaatgctg ctttcggctt gctacaatta | 720 |
| gaacatatgg atacttttct acgtggtcga atgaatgctg acatgttta tcggcagaaa | 780 |
| cttaaagata tcactggtat aagcatagta attcccagcg gccagaaaat atcgaatttt | 840 |
| tcatatttcc ctatattggt tgaatctgat tttccgttat ctcgtgatga actatttaat | 900 |
| tatctgaaga accagaatat ttttgcaaga cgttattttt atcctgttat accagatttt | 960 |
| caagcgtatt tgaatgtagg tgaagtctgt gatgtcaaga atgcccgtga aatagcctcg | 1020 |
| aaagtgctttt gcctaccgat gcatgcagaa ttgagctctg atatcttaga atatattgta | 1080 |
| agtacgatta gggagattaa atga | 1104 |

<210> SEQ ID NO 86
<211> LENGTH: 891
<212> TYPE: DNA
<213> ORGANISM: Artificial Sequence
<220> FEATURE:
<223> OTHER INFORMATION: Primer

<400> SEQUENCE: 86

| | |
|---|---|
| atggaaggaa cagttcctaa ggtctcagtc tgtgtgataa catataacca ggcgaaatat | 60 |
| ataaagcaat gcatagaaag cctaatcact caggactgtg atttcgatta tgaataattt | 120 |
| gtgagcgatg attgttcgac ggataataca cgagaaattt tagaacactt atatcatcaa | 180 |
| tatccagaaa agatacgtat atttatacat gaaaagaatc ttgggggttac taaaaattat | 240 |
| cttttcctgc atgaacaggc gcaaggcgag tatattgcac atgttgatgg tgatgactac | 300 |
| tattttcaa ataaattaag tttacaagca cgatatcttg atgaaaataa agagtgtaat | 360 |

```
attgtttggc atcctatgtt gttagataat aattcacgag tatttaatgg gtatcagcag    420
agtggaacta attttgtcga tttaaaattt actcaaggtg acataattca atatatttct    480
gtcggtaaaa acagctcaaa gatgtatcga aaaccgtac gagatattga tatacctgca    540
ttcgagctcg ttgactacct cgttaatgtt gaacaagttc agaatggcta tggtggatat    600
gcttcgaatg aacctctggg agtatatcga gtaggtgtag gaatttcatc ttctggagac    660
aaaactcgca ttgctcttcg ggatactttt ctttatctat taaaaaagta tccaaaatac    720
agattagaaa taaatacagc ggccttgaca tattttatcc gcgatatctt tgcaagaaga    780
aaatctgcaa agatttttt acatgtatgg ataaaaacgt ttcatcoctt ttcagtaatt    840 aaattactta aggggatgag tacaattaaa aaattaaaat atagagcata a             891

<210> SEQ ID NO 87
<211> LENGTH: 1125
<212> TYPE: DNA
<213> ORGANISM: Artificial Sequence
<220> FEATURE:
<223> OTHER INFORMATION: Primer

<400> SEQUENCE: 87
atgaaaaaga ttgtttttat aatcaataat gtcgattttt taatatctca tcgattacct     60
atcttactcg aggctcagaa aaatgggttt caggttcatg tgattgctcc taattccagg    120
aataatgagc tactaaagaa gcataaaata atgggtcatg atctctttct ttccagagga    180
ggtaataacc ctttttatga tttatttact ttgcttcagc ttacaaaaat tctgaaattt    240
ctcaagcccg accttgtcca tcttgtcacg attaaaccaa cactttatgg tgggattgct    300
gccagaatcg ccaaagtgcc tcatgtcgtt gcagctgtct ctgggctggg aaccgtattc    360
ttgagcagag gaatcatcag tggcttacgt cgcttactgg ttacaacctt gtatcactcc    420
gctctgaaac ataaaagaat acgcgttatc tttcagaacc ctgatgatcg tgagttactt    480
gtgagcgcag gcatattaaa ggtttccaat tcctgtctga tcagaggttc gggggttgat    540
ttaagagagt atccttatct tcctgaaaaa gttcacggta aaactgtagt aatggcctcc    600
aggctactaa gggataaagg ggtttatgag tttatcgaag ccgctcgctt acttaaacaa    660
aggaatgtag aggctgatat tagaatcatt ggttctccag atacctgtaa tccgacaagt    720
atcactgagg ctgaaataag caaatgggca tcagaaaata ttgttgaatt ctgcggattt    780
agaagtgaca ttgctaagca gtactctaat gctaatgtaa tatgcttgcc ctcatatcga    840
gaagggttac ctaaatgtct ggttgaagcc gcagcgtgtg gtagggcagt tgttacaact    900
gatgtaccag gttgcaggga tgcgatagtg gcaaatgtta ctgggatgtt agtcgcagtt    960
cgggatcctg tatcgttagc agatgcgatt gagtttctgc taaaaaatcc agatgaaaga   1020
ataaaaatgg ggaaggcggg gagattgtta gctgaaaatg agtactcaat cgaacatata   1080
gtgaatcagc acttatccat ttacaatgac ttaattcact cctga                  1125
```